United States Patent [19]

Ingrum et al.

[11] Patent Number: 5,002,397
[45] Date of Patent: Mar. 26, 1991

[54] SYSTEM OF FLUID INSPECTION AND/OR IDENTIFICATION

[75] Inventors: Jerry G. Ingrum, Fulton County, Ga.; Douglas J. Littlejohn, Santa Clara, Calif.; Douglas Modlin, San Mateo, Calif.

[73] Assignee: International Integrated Systems, Inc., Opelika, Ala.

[21] Appl. No.: 421,263

[22] Filed: Oct. 16, 1989

Related U.S. Application Data

[60] Continuation of Ser. No. 363,049, Jun. 8, 1989, which is a division of Ser. No. 181,160, Apr. 13, 1988, now abandoned.

[51] Int. Cl.[5] .................... G01N 21/31; G01N 21/85; B07C 5/10
[52] U.S. Cl. .................................. 356/407; 209/582; 250/226; 356/409; 356/411
[58] Field of Search ............... 356/240, 407, 409, 410, 356/411, 414; 250/223 B, 226; 209/524, 581, 582; 364/498

[56] References Cited

U.S. PATENT DOCUMENTS

| | | |
|---|---|---|
| 2,593,311 | 4/1952 | Johnson et al. . |
| 2,735,017 | 2/1956 | Beard et al. . |
| 3,266,292 | 8/1966 | Bailey .................................. 73/23 |
| 3,417,241 | 12/1968 | Davis . |
| 3,712,116 | 12/1973 | Andre .................................. 73/53 |
| 3,802,782 | 4/1974 | Natelson . |
| 3,827,812 | 8/1974 | Heimann ............................. 356/240 |
| 3,894,806 | 7/1975 | Remy et al. ......................... 356/240 |
| 4,055,252 | 10/1977 | Klamm et al. . |
| 4,087,184 | 2/1978 | Knapp et al. ...................... 250/223 B |
| 4,121,103 | 10/1978 | Calhoun ............................ 250/343 |
| 4,136,930 | 1/1979 | Gomm et al. ...................... 358/106 |
| 4,160,601 | 10/1979 | Jacobs ............................... 356/404 |
| 4,227,886 | 10/1980 | Bullock et al. . |
| 4,241,256 | 12/1980 | Tagaya et al. ..................... 250/223 |
| 4,262,196 | 4/1981 | Smith ............................... 250/223 B |
| 4,274,745 | 6/1981 | Takahashi et al. ................. 356/427 |
| 4,300,689 | 11/1981 | Franklin et al. ................... 209/524 |
| 4,303,342 | 12/1981 | Takahashi ......................... 356/427 |
| 4,367,041 | 1/1983 | Webb, Jr. et al. .............. 356/407 X |
| 4,368,980 | 1/1983 | Alfred et al. ...................... 356/240 |
| 4,402,612 | 6/1983 | Alexander et al. ................. 356/427 |
| 4,403,861 | 9/1983 | Buisde et al. ...................... 356/407 |
| 4,448,526 | 5/1984 | Miyazawa .......................... 356/237 |
| 4,488,648 | 12/1984 | Claypool ........................... 209/526 |
| 4,492,475 | 1/1985 | Takahashi ......................... 356/427 |
| 4,551,022 | 11/1985 | Tagaya .............................. 356/406 |
| 4,551,627 | 11/1985 | Reich ................................ 250/339 |
| 4,622,465 | 11/1986 | Harig et al. ....................... 250/373 |
| 4,650,326 | 3/1987 | Nagamine et al. ................. 356/240 |
| 4,766,551 | 8/1988 | Begley .............................. 364/498 |
| 4,830,192 | 5/1989 | Plester et al. ..................... 209/3.1 |
| 4,858,768 | 8/1989 | Plester ............................. 209/3.1 |

FOREIGN PATENT DOCUMENTS

| | | |
|---|---|---|
| 0067438 | 12/1982 | European Pat. Off. . |
| 2944434 | 3/1979 | Fed. Rep. of Germany . |
| 3245908 | 11/1982 | Fed. Rep. of Germany . |
| 133085 | 11/1978 | Japan . |
| 36733 | 3/1980 | Japan . |

OTHER PUBLICATIONS

Kajaan Electronics Ltd—Cormec Brightness Senson Information Sheet.
Eur-Control-Eur-Control BT-1 In-Line Brightness Transmitter Information Sheet.
Letter Dated Dec. 10, 1986, from Brian Devlin to Anheuser-Busch Inc.

Primary Examiner—Vincent P. McGraw
Attorney, Agent, or Firm—Louis T. Isaf

[57] ABSTRACT

A Method and Apparatus for identifying and distinguishing fluids and for recognizing contamination of a fluid, which method and apparatus utilizes spectrographic analysis of control samples of known fluids and then spectrographic analysis of unknown fluids to generate optical signatures, finger prints and/or profiles of data and processed data relating to the relative intensities of light at selected wavelengths; and then, through comparison of the various signatures, fingerprints and/or profiles, provides determinative information as to contamination or non-contamination of the unknown fluids; after which appropriate operation control is effected and/or exercised.

52 Claims, 19 Drawing Sheets

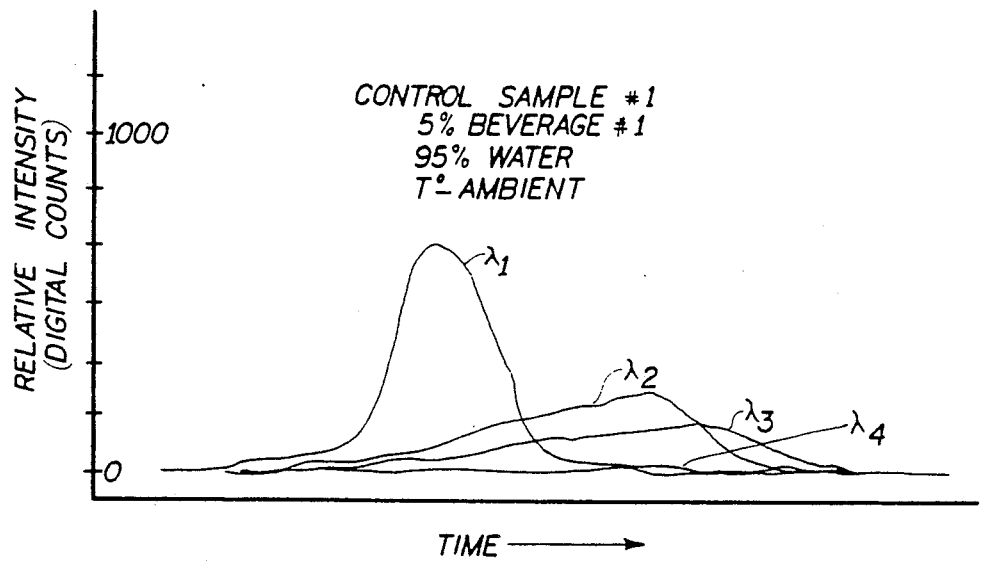

CONTROL SAMPLE #1
5% BEVERAGE #1
95% WATER
T°- AMBIENT

EXAMPLE PROCESSING $PI\lambda_1 = 803$     $PI\lambda_2 = 253$     $PI\lambda_3 = 157$     $PI\lambda_4 = 11$ $\Sigma I\lambda_1 = 8565.6$     $\Sigma I\lambda_2 = 4487.8$     $\Sigma I\lambda_3 = 2936.5$     $\Sigma I\lambda_4 = 215$

FIRST NORMALIZATION- $$(A): \frac{PI\lambda_2}{PI\lambda_1} = .3151 \quad (B): \frac{PI\lambda_3}{PI\lambda_1} = .1955 \quad (C): \frac{PI\lambda_4}{PI\lambda_1} = .0137$$

$$(D): \frac{\Sigma I\lambda_2}{\Sigma I\lambda_1} = .5239 \quad (E): \frac{\Sigma I\lambda_2}{\Sigma I\lambda_1} = .3428 \quad (F): \frac{\Sigma I\lambda_4}{\Sigma I\lambda_1} = .0251$$

SECOND NORMALIZATION- $$(G): \frac{(B)}{(A)} = .6204 \quad (H): \frac{(C)}{(A)} = .04347 \quad (I): \frac{(E)}{(D)} = .6543 \quad (J): = \frac{(F)}{(D)} = .0479$$

FIG 10A

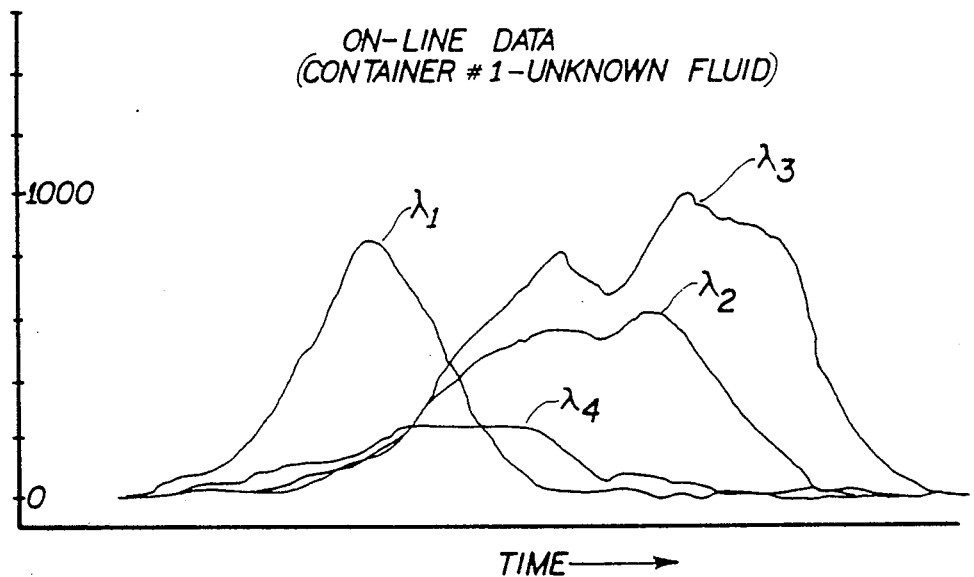

ON-LINE DATA
(CONTAINER #1-UNKNOWN FLUID)

EXAMPLE PROCESSING $PI\lambda_1 = 868 \quad PI\lambda_2 = 635 \quad PI\lambda_3 = 1033 \quad PI\lambda_4 = 259$ $\Sigma I\lambda_1 = 12005.83 \quad \Sigma I\lambda_2 = 14298.33 \quad \Sigma I\lambda_3 = 25563.83$ $\Sigma I\lambda_4 = 5893.17$

FIRST NORMALIZATION (A): $\dfrac{PI\lambda_2}{PI\lambda_1} = .7316$ (B): $\dfrac{PI\lambda_3}{PI\lambda_1} = 1.1901$ (C): $\dfrac{PI\lambda_4}{PI\lambda_1} = .2984$ (D): $\dfrac{\Sigma I\lambda_2}{\Sigma I\lambda_1} = 1.1909$ (E): $\dfrac{\Sigma I\lambda_3}{\Sigma I\lambda_1} = 2.1293$ (F): $\dfrac{\Sigma I\lambda_4}{\Sigma I\lambda_1} = .4909$

SECOND NORMALIZATION (G): $\dfrac{(B)}{(A)} = 1.6267$ (H): $\dfrac{(C)}{(A)} = .4079$ (L): $\dfrac{(E)}{(D)} = 1.7880$ (J): $\dfrac{(F)}{(D)} = .4122$

FIG 12

SYSTEM OF FLUID INSPECTION AND/OR IDENTIFICATION

This application is a continuation of application Ser. No. 07/363,049, filed Jun. 8, 1989 which is a division of 07/181,160, filed Apr. 13, 1988 abandoned.

FIELD OF INVENTION

The present invention relates generally to the field of spectrographic analysis of fluids and more particularly to the fields of contaminant detection and fluid identification, with emphasis on the bottling industry.

BACKGROUND OF THE INVENTION

The bottling industry is faced with many problems in the control and maintenance of their bottling facilities and procedures; but specific problems or concern herein are problems related to the "contamination" of the bottled products. The term "contamination" is used herein as meaning that any substance other than the intended "non-contaminants" (for example, the pure product and non-contaminating cleansers) is being, has been or will be introduced into the bottle or other container distributed to the consumer. A look at two, typical bottling procedures will help identify more clearly some example problems.

A first procedure which gives rise to concern about contamination is the actual bottle filling procedure. Probably more than a few bottlers have experienced the wasting of many hundreds of gallons of product because a container was filled with improper product. For example, some bottlers will, in the course of a day, utilize the same conveyor and piping systems to fill bottles or cans of two, three or more products. The system will first be used, for example, to fill product 1 containers, then product 2, then product 3, and so on. For example, some beer manufacturers have procedures of utilizing the same conveyor and piping system to ultimately fill containers of premium beers, non-premium beers, and low calorie ("light") beers. If the wrong product is introduced into a particular container, then that product is "contaminated". This is one type of contamination problem. Such contamination can occur either by operator error, in which the operator simply directs product from the wrong storage tank into the piping system, or when there is "residue" from a prior product run remaining in the piping system.

A second procedure which gives rise to concern about contamination is the "refilling" procedure. This is a procedure in which the bottler collects used bottles, refills and reuses these bottles to contain fresh products. Usually these containers were used by consumers to simply dispense of the original product and were then returned to a collection facility. However, the consumer may have used the container to hold a substance other than the original product and then delivered the container at some later time to the collection center. A bottler must be concerned about whether an incoming container has been used to hold any substance which would affect the quality (i.e. taste or smell) of its product. This potential for contamination of "refillable" bottles is of particular concern when refilling plastic bottles. The concern of refilling plastic, refillable bottles is the possibility that contaminants have been absorbed into the walls of the bottles and then leach into fresh liquid product subsequently placed in the refillable bottles. Because of the absorption and leaching problem, a bottler would rather identify a plastic bottle that has been used to hold a contaminated foreign substance and discard that bottle, rather than attempt to clean and reuse that bottle.

For many years, the industry has sought to address the contamination problem mentioned above. With respect to the first bottle filling procedure mentioned above, some bottlers may have dealt with the contamination problem by, on the one hand, simply accepting the fact of human error and throwing away mis-filled containers; and on the other hand, utilizing excessive amounts of pure product or water to "flush" the pipeline of prior fluids. In this "flushing" technique, a great deal of waste results because the bottler is not positive of the point at which the system has been purged of prior fluids and, thus, purges excessive amount of pure product in order to be certain of clean lines.

In addressing the contamination of refillable plastic bottles, the industry has tested several techniques in the laboratory which have varying degrees of success or failure.

SUMMARY OF THE INVENTION

Briefly described, the present invention comprises a method, with accompanying apparatus, for inspecting a fluid and determining whether or not the fluid contains contaminants. The term "fluid" is to be broadly interpreted and shall include, without limitation, liquids, solutions, slurries and mixtures. In its preferred embodiment, the present invention spectrographically analyses control samples of a known fluid, which known fluid is considered by the user to be "non-contaminated". The spectrographic analysis of the control sample is utilized to identify relative intensities of light at a plurality of pre-selected wavelengths. The relationship of relative light intensities at the given wavelength is used to identify the non-contaminated fluid. Then, in order to determine whether or not an unknown fluid is "contaminated", the unknown fluid (also referred to as the "on-line fluid") is tested by performing a spectrographic analysis of the unknown fluid to acquire data as to the relationship of relative light intensities at the same wavelengths used to identify the control samples. By comparing data taken of the on-line fluid to data of the control fluid, a determination is made as to whether or not the on-line fluid is contaminated.

In one species of the preferred embodiment, the invention addresses the problem of refillable, plastic containers. In the preferred embodiment of this "refillable container species", the container, such as a refillable plastic bottle, contains an on-Line fluid, the exact make-up of which is completely or partially unknown. The bottle, with the on-line fluid therein, is moved past a light source. Light from the light source is absorbed by the bottle and the on-line fluid and resulting, unabsorbed light is collected either by transmission, reflection or transflection at a light detector. The collected light is divided and filtered into a plurality of separate light beams, each at a different wavelength. In the preferred embodiment, collected light is divided into four or more wavelengths. Data relating to the relative intensity of light at each of the wavelengths is collected, processed and compared to similar data from control samples. If the on-line fluid does not compare favorably with the control sample data, the respective container is considered to have contained contaminant and is rejected.

In an alternate species of the preferred embodiment, known as the "Flying Brand Species", the on-line fluid, assumed to be unknown, passes within a fluid container, such as a conduit, past an observation port within the conduit. A light source directs light through the observation port and the light is absorbed by the transparent port and the passing test fluid. Unabsorbed light from the light source is collected by transmission, reflection or transflection at a light detector. The collected light is separated and filtered into a plurality of light beams, each at a different wavelength. Data is collected and processed relating to the relative intensity of the collected light at each of the wavelengths. The test data is compared to similarily collected and processed control data relating to and identifying the known fluid of a control sample. If the test data does not favorably compare with the control data, the on-line fluid is considered contaminated and directed away from the containers to be filled or toward alternate containers if appropriate. If the test and control data favorably compare, on-line fluid is considered non-contaminated, is considered to be the "proper product", and is directed to the awaiting containers.

In preferred embodiments of the present invention, control data is taken from a plurality of control samples. Each control sample varies from the other control samples in one or more of its properties, such as but not limited to concentration level, temperature, container condition (i.e. scratches), and dirt content.

The aforementioned methods of the present invention are preferably performed through what shall be termed an electro-optical sensing apparatus which includes, generally, a fluid transporting mechanisim, a light emitting module, a light detector and transmission module, a plurality of filter/amplifier modules a data acquisition and storage device for acquiring and storing light intensity data related to each of the filter/amplifier modules; and computer device (1) for calculating relationships among the collected data, (2) for comparing on-line and control data, (3) for determining acceptability of the compared data, and (4) for activating appropriate reject or control mechanism.

It is, therefore, an object of the present invention to provide a method of idenfifying contamination of a fluid.

Another object of the present invention is to provide a method for discriminating among the various substances that may or may not be present in transparent containers.

Still another object of the present invention is to provide a method of providing system control signals to effect rejection of a recycled container upon the discovery of contaminant present in the container.

Another object to the present invention is to provide systems control signals for affecting fluid flow to direct "contaminated" products away from awaiting containers and to direct "non-contaminated" products into awaiting containers.

Still another object of the present invention is to provide an apparatus for performing the aforementioned methods.

Still another object of the present invention is to provide method and apparatus for reliably identifying a fluid through the use of spectrography.

Another object of the present invention is to provide a method and apparatus for identifying and distinguishing fluids through the use of optical signatures, finger prints, and/or profiles acquired through the use of spectrographics.

Yet another object of the present invention is to provide method and apparatus for the purpose of "on-line" substance detection; and qualification, quantification or discrimination among various substances that may or may not be present in re-fillable containers constructed of plastics, glass, ceramic, metal, latex cellulose or other materials of construction, such as, but not limited to, cans, bottles, jars, bowls, tubes, boxes or bags, and uniquely integrating the container into the system optics.

Another object of the present invention is to provide a fluid inspection and identification apparatus used as a primary sensing element in process control or quality control applications as a primary sensing element in servo feed-back or feed forward techniques and used to divert flows, control flows, meter additions and institute other process control or process logic functions.

Other objects, features and advantages of the present invention will become apparent upon reading and understanding this specification, when taken in conjunction with the accompanying drawings and attachments.

BRIEF DESCRIPTION OF DRAWINGS, CHARTS AND GRAPHS

FIGS. 10A-10F are plotted representations of Control Data acquired from a plurality of Control Samples, in accordance with the Refillable Container Species embodiment of FIG. 6, and showing specific examples.

FIG. 12 is a plotted representation of On-line Data acquired from an On-line Sample, in accordance with the Refillable Container Species embodiment of FIG. 6, and showing a specific example.

DETAILED DESCRIPTION OF THE PREFERRED EMBODIMENT

Detailed description is now provided for preferred embodiments of the method and associated apparatus which comprises the system of the present invention; and, where appropriate, reference is made to accompanying drawings in which like numerals represent like components throughout the several views.

Figure 1:
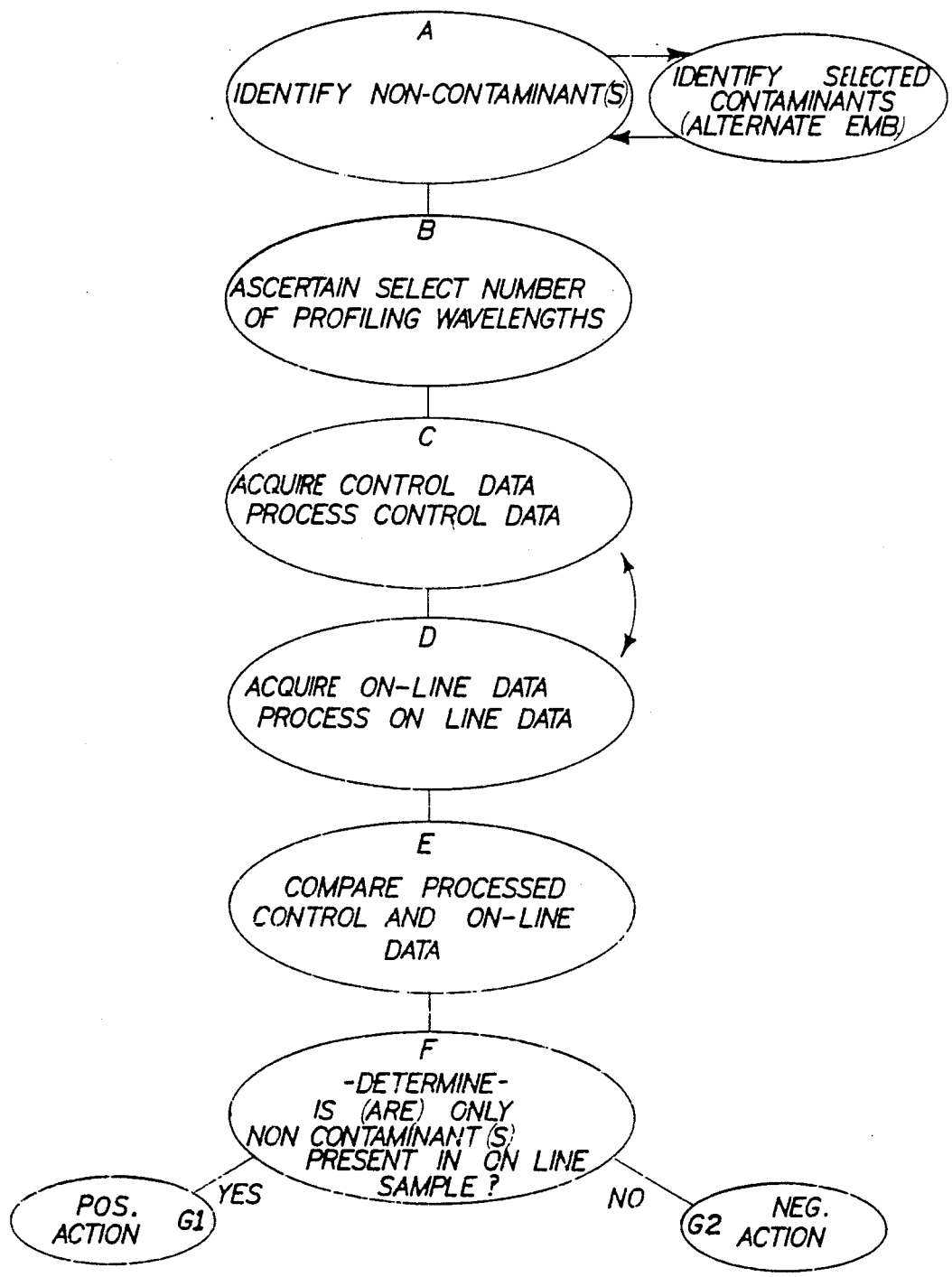
FIG. 1 is a flow diagram representing an overview of a fluid inspection and/or identification method in accordance with the present invention.

An overview of the process of the present invention is seen in FIG. 1. A first step in the process is to identify what the user will consider to be a non-contaminant (Step A). Substances other than such an identified non-contaminant are to be considered, for purposes of the invention, as contaminants. The user will identify a group of substances or a single substance as the non-contaminant(s). By way of example only, and without limitation, such a group of non-contaminants may include a family of nonalcoholic, carbonated beverages; such as, cola, grape, lemon-lime, diet cola, etc. As another example, without limitation, the non-contaminant may be a single product such as a specific nonalcoholic beverage or a specific beer. In alternate embodiments, the user may choose to include, in the group of non-contaminants, water, dirt or other substances subjectively determined to be non-contaminants. At the same time, in alternate embodiments, the user selects a number of substances which, if present in fluid, will be considered contaminates. By way of example only, and without limitation, such contaminants may include substances such as household chemicals, agricultural chemicals, alcohols, solvents and petroleum products, etc. As other examples, without limitation, the contaminant may be a product such as a cola or a selected group of non-alcoholic beverages (such as when a lemon-lime beverage is the sole, identified non-contaminant) or low-calarie beer (such as when premium beer is the sole, identified non-contaminant). It is understood that the substances identified as non-contaminants will vary at the discretion of the user, and, what may be chosen as a non-contaminant in one circumstance may be chosen as a contaminant in another circumstance, and visa-versa.

Figure 2:
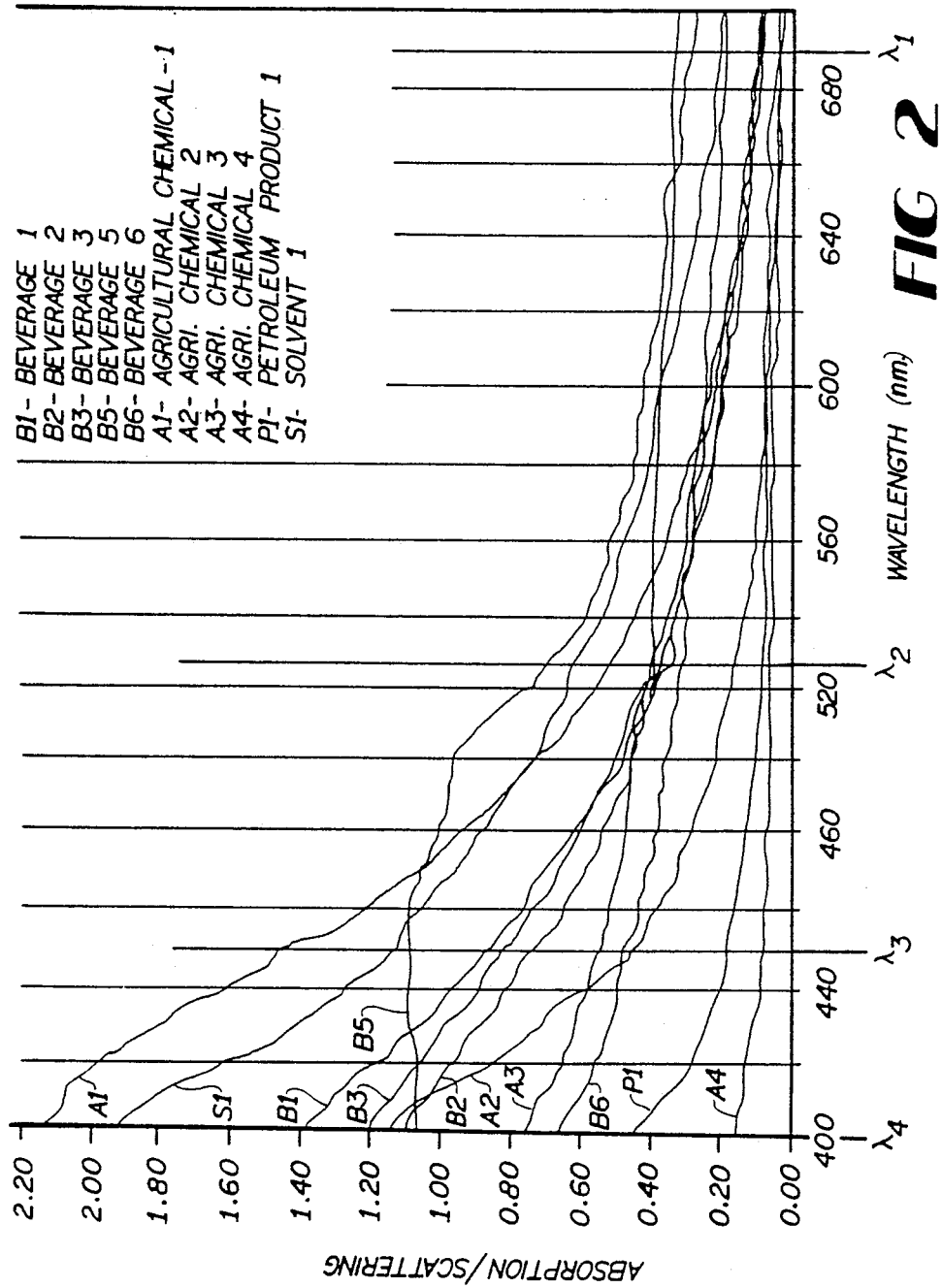
FIG. 2 is a plotted representation of light absorption/scattering over a range of wavelengths showing spectrographic analysis utilized to choose profiling wavelengths in accordance with the present invention, showing specific curves for example purposes only.

Once non-contaminants and select contaminants have been identified, the user ascertains a plurality of wavelengths (Step B), preferably in the visible spectrum, which the user considers the most optimum in providing a unique spectral profile of each non-contaminant. Reference is made to FIG. 2. Such "profiling wavelengths" ($\lambda 1 - \lambda n$) are chosen, for example, by determining wavelengths along the spectrum at which the absorption/scattering curves of the various non-contaminants within the group are distinguishable from the absorption/scattering curves of all other non-contaminants within the group and/or are distinguishable from the absorption/scattering curves of all of the selected contaminants. Although use solely of the visible spectrum wavelengths is preferred, in certain applications, UV and IR wavelengths are used where necessary to augment. It is preferred that at least four profiling wavelengths be utilized and also that the number of profiling wavelengths be kept as low as possible, preferably four or five, in order to hold down costs of the associated apparatus while still clearly identifying those substances in question. If cost is of no consequence, a greater number of profiling wavelengths can be chosen. Computer analysis, performed in one of many manners known in the industry, is utilized in some embodiments to assist in optimally selecting the profiling wavelengths. The depicted profiling wavelengths shown on FIG. 2 are by way of example only, for use in the specific examples (below) of this specification; and the scope of the invention is not limited to or by the depicted example.

Figure 3:
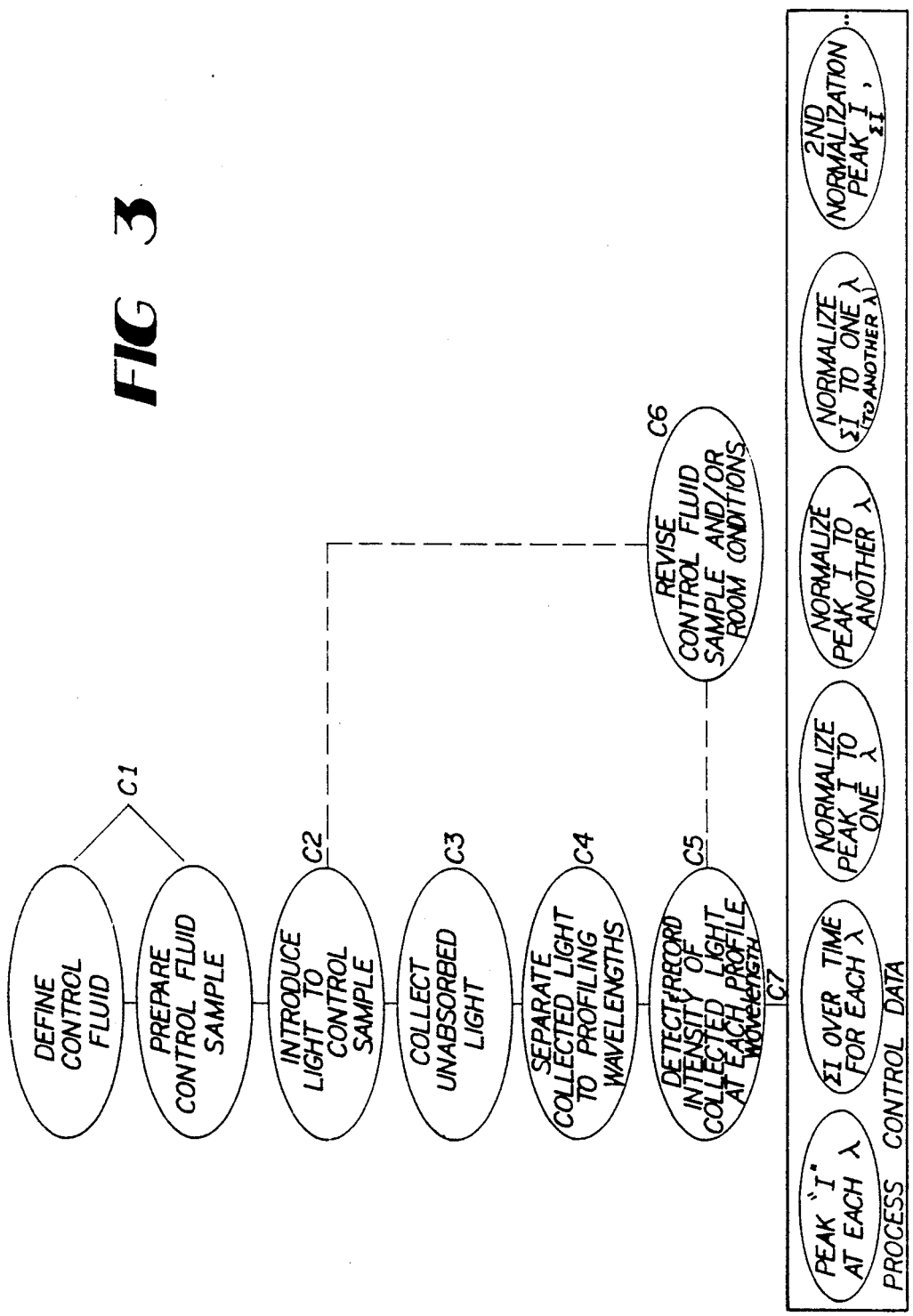
FIG. 3 is a flow diagram representing one embodiment of the method steps associated with step "C" of FIG. 1, "Acquire Control Data-Process Control Data".
Figure 5:
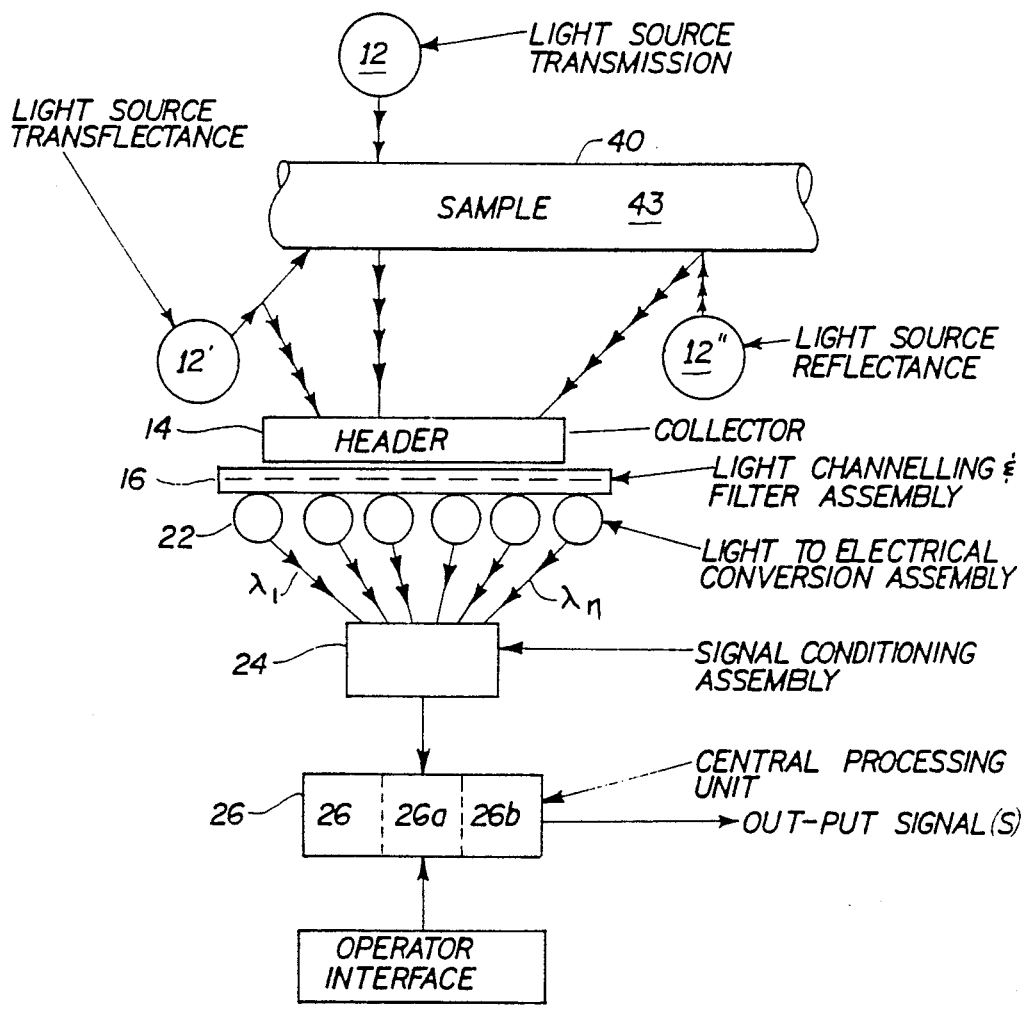
FIG. 5 is a schematic representation of a fluid inspection and/or identification apparatus in accordance with the present invention.
Figure 6:
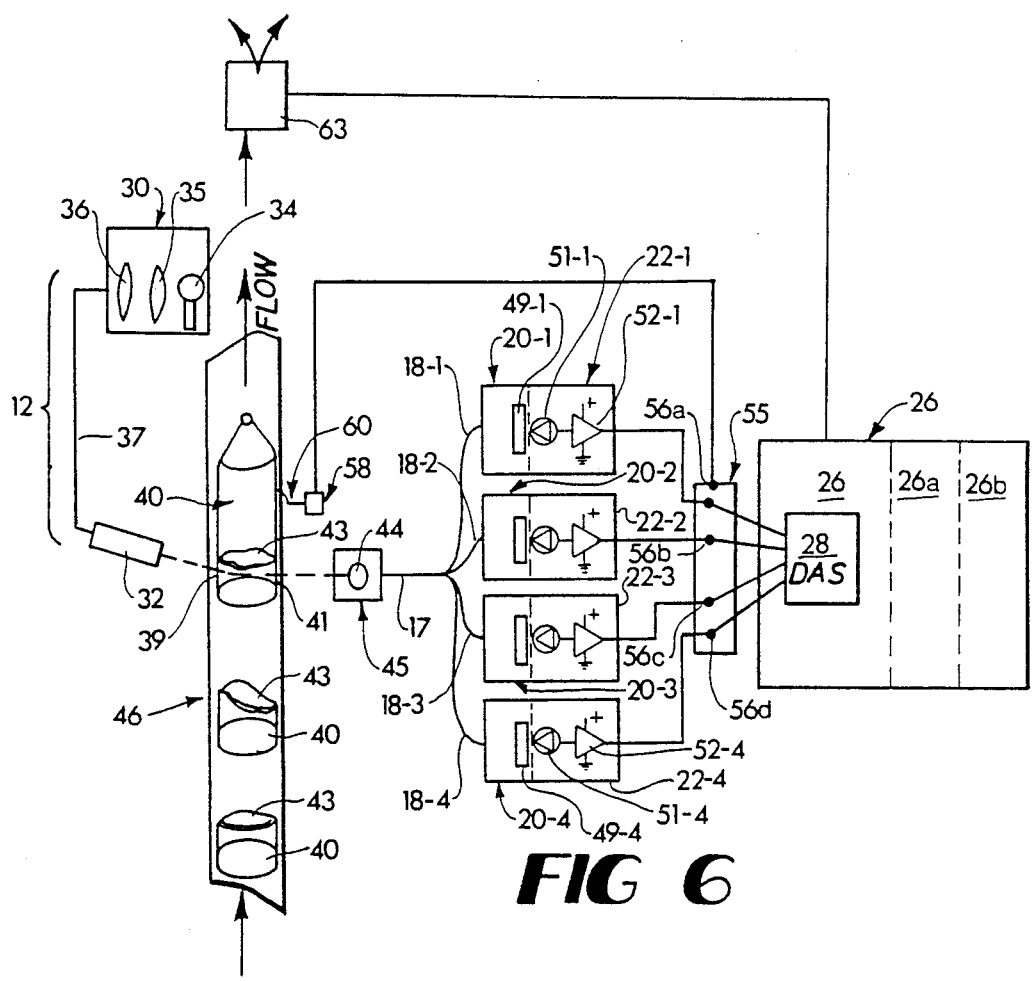
FIG. 6 is a schematic representation of the apparatus of FIG. 5, depicting one embodiment thereof, for application with a "refillable Container Species".

Once the user has identified the chosen non-contaminant(s) and ascertained the profiling wavelengths, data is acquired in accordance with the present invention (Steps C & D). Although it is acceptable within the present invention to take "on-line" data prior to control data, the preferred embodiment calls for first acquiring control data. With reference to FIG. 3, the user now defines the "Control Fluid". The Control Fluid is a fluid consisting of one of the identified non-contaminants in either full strength or in varied concentrations with one or more other acceptable non-contaminants. For a better understanding, attention is directed to the examples given below. A sample of the Control fluid is prepared from which data is to be acquired. The data to be acquired is data related to the absorption/scattering of light by the Control Fluid at each of the profiling wavelengths. Thus, the Control Fluid sample is exposed to light from a light source 12 (refer to FIG. 5) and some of the light is absorbed by the Control Fluid as will naturally occur in nature. The light which is not absorbed is scattered or continues through the fluid medium; and the non-absorbed light or a representative portion of the non-absorbed light is collected, as much as possible, by appropriate collectors 14. In alternate embodiments, the non-absorbed light collected is either transmitted light or reflected light or a combination thereof ("Transflected light"). The collected light is then separated such that collected light at each of the profiling wavelengths is isolated. The apparatus for accomplishing this is represented by block 16 of FIG. 5, marked "light channelling and filter assembly". In preferred embodiments, as depicted in FIG. 6, this isolation of profiling wavelengths is accomplished by dividing the collected light into a plurality of light beams by one of numerous methods known in the art, including, but not limited to (1) focusing the collected light on a plurality of separate fibers 18-$l$ . . . 18-$n$ of a multifiber, fiber optic cable 17, each fiber representing one of the plurality of light beams, or (2) focusing the collected light on a single fiber optic cable 17 which is subsequently split, by known methods, into a plurality of strands 18-$l$ . . . 18-$n$, each communicating the collected light equally, or (3) by direct lensing of the light information. Each of the light beams of the embodiment of FIG. 6 is filtered at a separate filter module 20-$l$ . . . 20-$n$ to provide the preferred, isolated light at only one of the selected profiling wavelengths.

Figure 7:
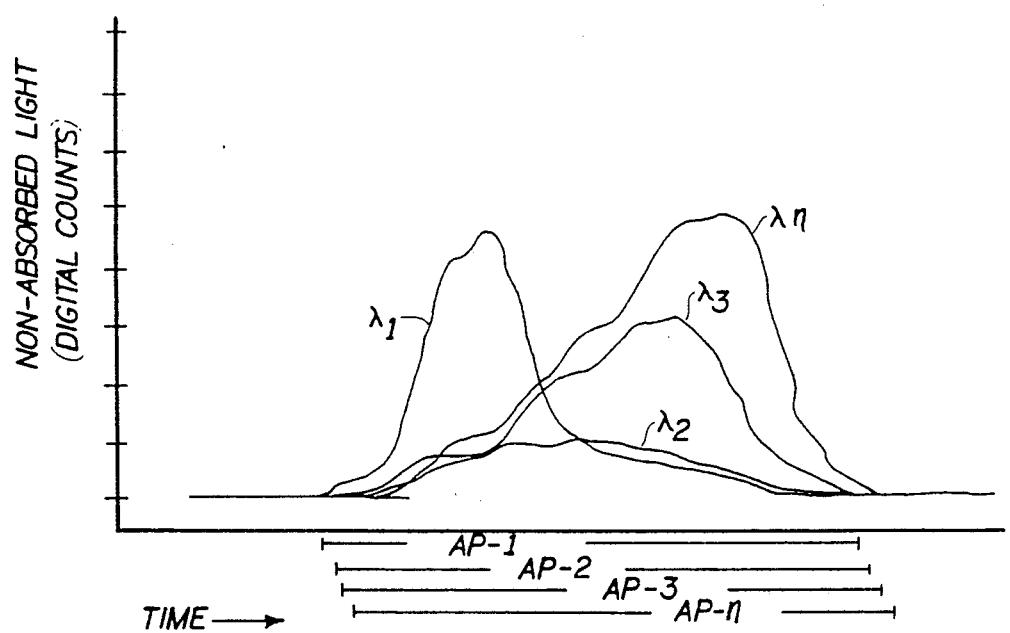
FIG. 7 is a plotted representation of light intensity data acquired from a fluid sample (either Control Sample or On-line Sample), over a period of time, at each of the selected, profiling wavelengths, in accordance with the present invention, as such data is generated by the Refillable Container Species embodiment of FIG. 6.
Figure 7A:
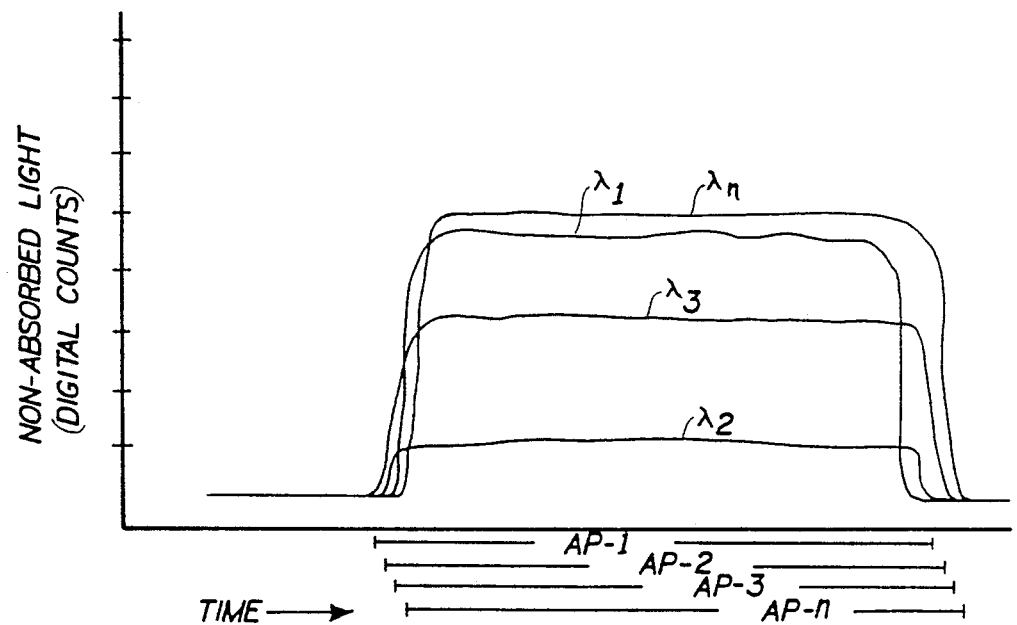
FIG. 7A is a plotted representation of light intensity Data acquired from a fluid sample (either Control Sample or On-line Sample), over a period of time, at each of the selected, profiling wavelengths, in accordance with the present invention, as such data is generated by the Flying Brand Species embodiment of FIG. 6A.

The intensity of the collected light at each of the profiling wavelengths is detected by a detector 22 detecting the intensity of the light isolated at the respective profiling wavelength. This detecting of intensity is, in preferred embodiments, accomplished through conversion of the filtered light to an electrical signal representative of the intensity. Whereas, the absolute value of light intensity at the respective profiling wavelength is detectable and usable herein, preferred embodiments of the present invention detect relative values of the light intensity at each profiling wavelength, relative to an arbitrary base "0" and relative to one another. The term "intensity", when used throughout this specification and claims shall be understood to refer to relative intensity and/or absolute intensity. When appropriate, the respective electrical signal of each profiling wavelength is separately amplified for calibration purposes and for providing adequate resolution for manipulation of acquired data. Such amplification is represented in FIG. 5 by the signal conditioning assembly 24 and in FIG. 6, by the amplifier 52-1 . . . 51-4. The detected data of respective light intensity is recorded and then, preferably, stored by a device 26, such as a computer, functioning as a recording and storing device 26. In the preferred embodiments of the present invention, the intensity of collected light at each profiling wavelength is recorded at a plurality of points in time over a prescribed period of time. Acquired Data, both Control data and On-Line data, may be represented in tabulation form and/or plotted form. Representative examples of acquired data in plotted form are seen in FIGS. 7 and 7A. This will be better understood with reference to the apparatus described below. Although useful control data is provided from a single, properly prepared Control Fluid sample, it is preferred to obtain control data from a variety of different, revised Control Fluid samples and revised control conditions; that is, revised as to properties such as, but not limited to, concentration levels of chosen non-contaminates, temperature of the Control Fluid, room temperature and/or room pressure, container color/tint, and dirty or scratched containers. The "revising" is done in an effort to obtain data from at least some control samples which will more closely approximate the unpredictable properties and conditions of the on-line fluid when acquiring on-line test data in order to identify and isolate the effects of these properties. Thus, it is seen (at step C-6, FIG. 3) that the Control Fluid sample is revised in one or more of its properties (concentration, temperature, etc.) and then steps C-2 through C-5 are performed on the revised control sample. The Control Fluid sample is revised a number of different times, in a number of different ways, and, the intensity of collected light at each of the profiling wavelengths is detected and recorded and, preferably, stored along with indentifying parameters of each revision of the Control Sample. Hereinafter, the term "Control Sample(s)" shall refer individually and collectively to the originally prepared Control Fluid sample and each subsequent revision thereof. Examples of control data collected in accordance with two, below described applications (species) of the preferred embodiment are seen in graph form in FIGS. 10A-10F and FIG. 13.

The acquired control data is processed by a device 26$a$ such as a computer, functioning as a processing device 26$a$ to provide a plurality of mathematical interrelationships among the light intensity data associated with the respective, profiling wavelengths for each Control Sample. The processing provides a number of interrelationships which include, but are not limited to, one or more of the following: peak intensities ($PI\lambda_1$, . . . $PI\lambda_n$) for each profiling wavelength over the data acquisition period; maximum average intensity for each profiling wavelength ($AvI\lambda_1$, . . . $AvI\lambda_n$), which is acquired by summing the intensities over the acquisition period and then dividing by the number of data acquisition points in the data acquisition period; sum of the intensities over the acquisition period for each profiling wavelength ($\Sigma I\lambda_1$, . . . $\Sigma I\lambda_n$); the ratios of the aforementioned relationships for each profiling wavelength to one of the profiling wavelengths, for example, but without limitation, $PI\lambda_2/PI\lambda_1$, $PI\lambda_3/PI\lambda_1$, $PI\lambda_n/PI\lambda_1$, $AvI\lambda_2/AvI\lambda_1$, $AvI\lambda_3/AvI\lambda_1$, $AvI\lambda_n/AvI\lambda_1$, $\Sigma I\lambda_2/\Sigma I\lambda_1$, $\Sigma I\lambda_3/\Sigma I\lambda_1$, $\Sigma I\lambda_n/\Sigma I\lambda_1$, $PI\lambda_1/PI\lambda_n$ . . . $PI\lambda_{n-1}/PI\lambda_n$, $AvI\lambda_1/AvI\lambda_n$ . . . $AvI\lambda_{n-1}/AvI\lambda_n$, $\Sigma I\lambda_1/\Sigma I\lambda_n$ . . . $\Sigma I\lambda_{n-1}/\Sigma I\lambda_n$, etc. (defined for purposes hereof as "First Normalization"); plotting of the aforestated ratios; ratios of the ratios, for example, but not limited to, $[PI\lambda_3/PI\lambda_1]/[PI\lambda_2/PI\lambda_1]$, $[PI\lambda_n/PI\lambda_1]/[PI\lambda_2/PI\lambda_1]$, $[PI\lambda_2/PI\lambda_1]/[PI\lambda_3/PI\lambda_1]$, $[PI\lambda_n/PI\lambda_1]/[PI\lambda_3/PI\lambda_1]$, $[PI\lambda_2/PI\lambda_1]/[PI\lambda_{n-1}/PI_n]$ . . . $[PI\lambda_{n-2}/[PI\lambda_{n-1}]/[PI\lambda_{n-1}/PI\lambda_n]$, etc. (defined for purposes hereof a "Second Normalization"); plotting of these ratios of ratios. The processed data is recorded (and stored) at the recording/storing device 26 in tabulated form or in graphic form for each Control Sample. It is noted that the tabulated, processed data translates in graph form to a collection of "topographies" which "fingerprint", "profile" or "signature" the Control Fluid across the varied, revised properties of the control samples. For examples of such processed data, see graphs of FIGS. 11A-11D, 14A-14C. The "topographies" of FIGS. 14A-14C contain only a single signature since, in that specific example, no revisions were made to control Fluid samples; as is an acceptable embodiment where conditions allow. The process steps (C7, FIG. 3) are shown as performed as part of the step of acquiring data, but it is understood that the processing steps are performable, in alternate embodiments, at a later step, ie., in conjunction with the comparing step (step "E").

The next step of FIG. 1 is the step of acquiring on-line data (step "D"). The on-line data is, preferably, acquired by a method (see FIG. 4) similar to that used for acquiring control data. In the preferred embodiment, the on-line data is acquired utilizing apparatus identical to that apparatus utilized to acquire the control data. To acquire on-line data means, herein, to acquire data associated with a fluid which is being tested, for example, in the course of user's daily business operation, to determine if it contains contaminants. That is, the "On-Line Fluid" is being tested to determine if substances other than the chosen non-contaminants of the control fluid are present in the On-Line Fluid. The On-Line Fluid is first "prepared". This means that the fluid to be tested is prepared in some manner for the introduction of light (step D2). Preparation will vary depending upon the particular application, and various preparations include, without limitation, placing of a fluid, as is, in a container or conduit and/or by adding a known non-contaminant (such as, for example, water) to substance(s) already in the container and/or simply checking the container to see if fluid already exists in the container in sufficient quantity to be acted on in the next step. See descriptions of the two, example applications (species) mentioned below.

Figure 4:
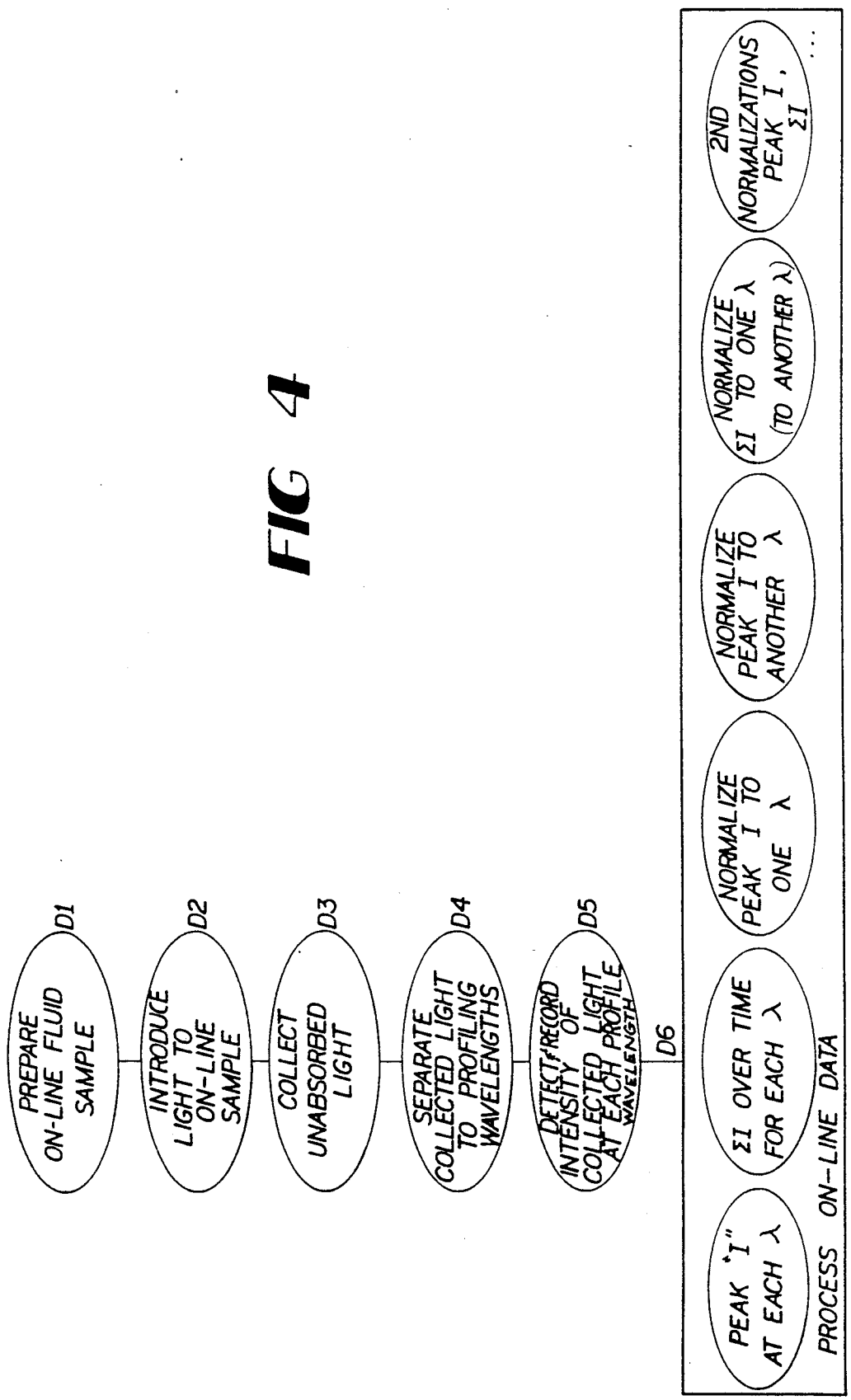
FIG. 4 is a flow diagram representing one embodiment of the method steps associated with step "D" of FIG. 1, "Acquire On-line Data-Process On-line Data".

Once the On-line Fluid has been prepared, light is introduced to the fluid (D2, FIG. 4). In the preferred embodiment, the step of introducing light to the On-line Fluid is performed in a manner substantially identical to the step of introducing light to the control fluid, or visa-versa. That is, the Control Fluid and On-line Fluid are both passed by the light source as a flowing fluid within a conduit; or, the Control Fluid and On-line Fluid are both held within a container of similar configuration and make-up, which container moves past the light source; or, for example, the Control Sample and On-line Sample are each held within a container of similar configuration and make-up and the light source is moved past the container. Furthermore, in the preferred embodiment, the same optical instrument is utilized to obtain control data as is utilized to obtain On-line data in order to promote uniformity of resultant data, although in less acceptable, alternate embodiments, different but substantially similar apparatuses are utilized to acquire the control data and On-line data, respectively. Thus, utilizing the apparatus of the present invention, in accordance with the method described with respect to acquiring control data, light is introduced to the On-line Fluid and the non-absorbed light is collected, as much as possible, by the appropriate collectors 14, by the same method of transmittance, reflectance, or transflectance as utilized in acquiring control data. The collected light is then separated at the appropriate light channelling and filter assembly 16 such that the collected light at each of the profiling wavelengths is isolated. The intensity of the collected light at each of the profiling wavelengths is detected by the respective detector 22 (FIG. 6) and, preferably, converted to an electrical signal representative of the respective intensity. Since it is desired to pass judgment on this On-line Fluid as to the presence or absence of contaminants, there is no step corresponding to the "revise control fluid sample" step C6 of FIG. 3. In the preferred embodiment, the intensity of collected light at each profiling wavelength is recorded at a plurality of points in time ("data acquisition points") over a prescribed period of time ("data acquisition period"), in a manner similar to the corresponding step in the acquisition of control data. The acquired, On-line data is processed by the processing device 26a to provide a plurality of mathematical inter-relationships among the light intensity data associated with respective, profiling wavelengths for the On-line Fluid. The processing provides a number of inter-relationships which correspond to inter-relationships of the processed Control Data, such as, but limited to, one or more of the peak intensities, maximum of average intensities, Sum of intensities, first normalization of data to one (or to each) of the profiling wavelengths, second normalization, and plotting of the same. For examples of such processed data, see charts 3A, 3B and graphs 18A and 18B. As mentioned above, the processing steps are performable, in alternate embodiments, at a later step, ie. in conjunction with the comparing steps ("E").

The next step in FIG. 1 is to compare processed control and On-line data (Step E). This comparison is performed, in alternate embodiments, by manual and visual techniques or, in preferred embodiments by a device 26b, such as a computer, functioning as a comparator. One method, being a perfered method, of comparing the processed On-line data to the processed control data is to compare the plotted signatures for processed On-line data to the topographies for corresponding, processed control data. Utilizing the various, known techniques of "catagory theory", the comparator 26b (or user) seeks to "fit" the On-line data signature in the corresponding control data topography. If the On-line signature "fits", it is determined (step F) that only non-contaminant is present. If the On-line signature does not "fit", it is determined that substance other than (or in addition to) the non-contaminant are present in the On-line Fluid. In order to enhance the chances of successful determination, the preferred method requires that the signature of each of the inter-relationships derived from the On-line data (signature of FIGS. 12A–12D, FIGS. 15A–15C) "fit" the topographies of the corresponding inter-relationships from the control data or "fit" predicted topographies of control data which are based on the control data via known methods of interpolation. If any one of the On-line data signatures does not "fit" the corresponding data topography, the On-line Fluid is determined to contain contaminants. As represented by step G1, if it is determined that only non-contaminants are present in the On-line Fluid, the apparatus of the present invention provides a control signal which dictates a "positive action" with respect to the On-line Fluid and/or its related container. The positive action translates into, for example but not limited to, "keep the container", or "divert fluid flow to awaiting packaging". In accordance with step G2, if it is determined that something other than (or in addition to) non-contaminants is present in the On-line Fluid, the apparatus of the present invention provides an output signal which dictates a "negative action". Such negative action translates into, for example but not limited to, command to a reject mechanism to "reject the container" or "divert fluid flow to purge the On-line Fluid".

Having described in detail the preferred method of the present invention, and having generally described the apparatus associated therewith, attention is now directed to specific applications (or species) of the previously described method and apparatus. Whereas other applications and embodiments are within the scope of the present invention, the following will concentrate on two applications which particularly point out two, presently, best known, species of the present invention. The two applications are termed: (1) "refillable container species" and (2) "flying brand species".

The "refillable container species" comprises a unique application of the method and apparatus of the present invention to identify, tag, and provide a signal for a rejection mechanism to discard clear or tinted plastic bottles, which plastic bottles were being returned to a bottling plant for refilling, and which bottles have been contaminated by any foreign substances; that is, had been used to store substances other than the product (the non-contaminant) with which the container had been originally filled. The "flying brand species" comprises a unique application of the apparatus and method of the present invention for determining whether or not the fluid flowing through a piping system is that exact fluid which the user intended to be pumping through the conduits. The intended fluid is the non-contaminant and any other fluid is the "contaminant". The flying brand change species also has application in determining when fluid flowing through a piping system has changed from fluid #1 to fluid #2. In such a brand change scenario, fluid #2 is the "non-contaminant" and fluid #1, or any substance other than fluid #2, is the contaminant. The apparatus of the present invention associated with the refillable container species is shown in schematic form in FIG. 6. The apparatus of the present invention associated with the flying brand change species is shown, in schematic form, in FIG. 6A. It is noted that the apparatus of both species are similar and, therefore, the common apparatus will be discussed below and reference, when appropriate, will be made to the distinguishing aspects of the apparatus for each species.

Figure 6A:
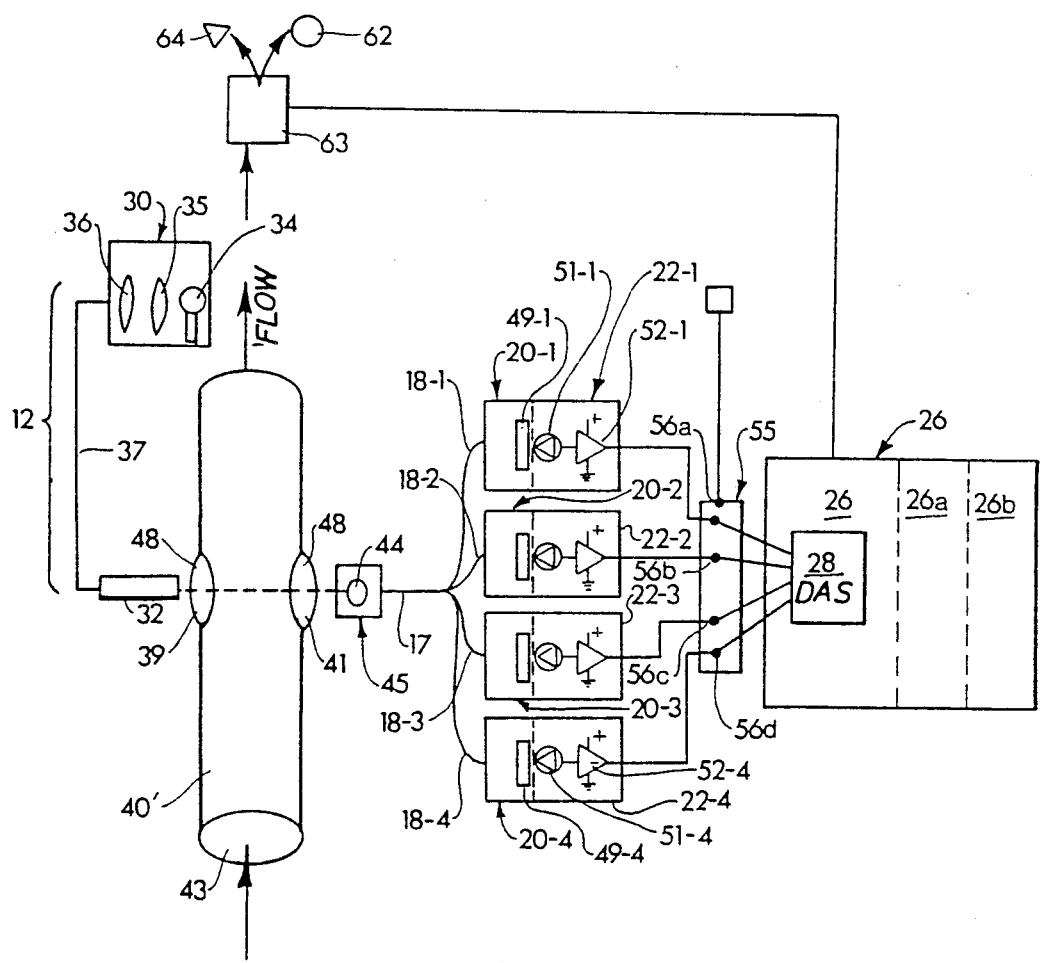
FIG. 6A is a schematic representation of the apparatus of FIG. 5, depicting an alternate embodiment to that of FIG. 6, for application with a "Flying Brand Species".
Figure 9:
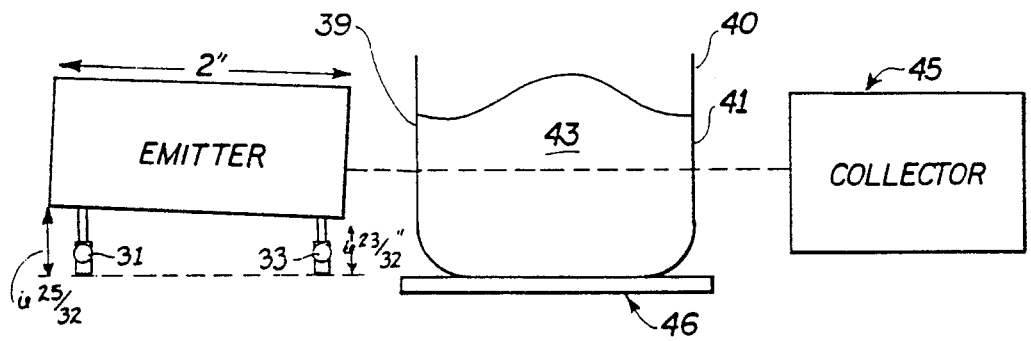
FIG. 9 is a schematic, side view, representation of a preferred orientation of an emitter module, container, and detector module in accordance with the embodiment of FIG. 6 of the present invention.
Figure 9A:
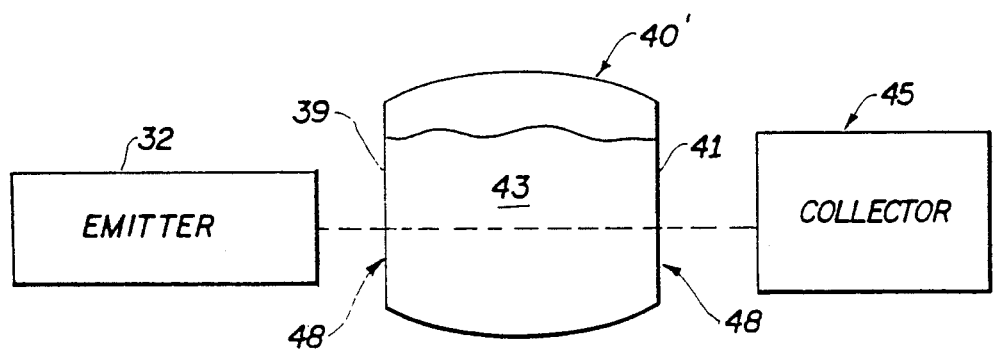
FIG. 9A is a schematic, side view, representation of a preferred orientation of an emitter module, conduit, and detector module in accordance with the embodiment of FIG. 6A of the present invention.
Figure 10B:
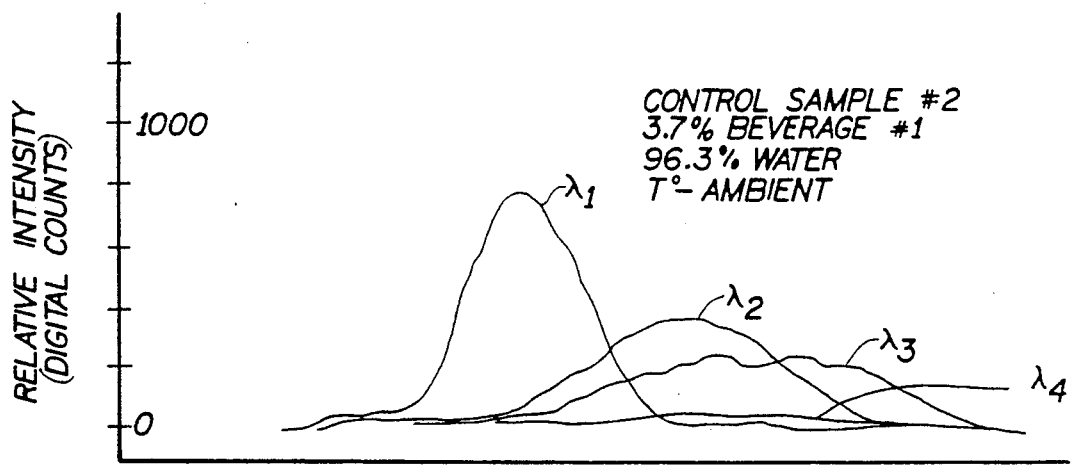
Figure 10C:
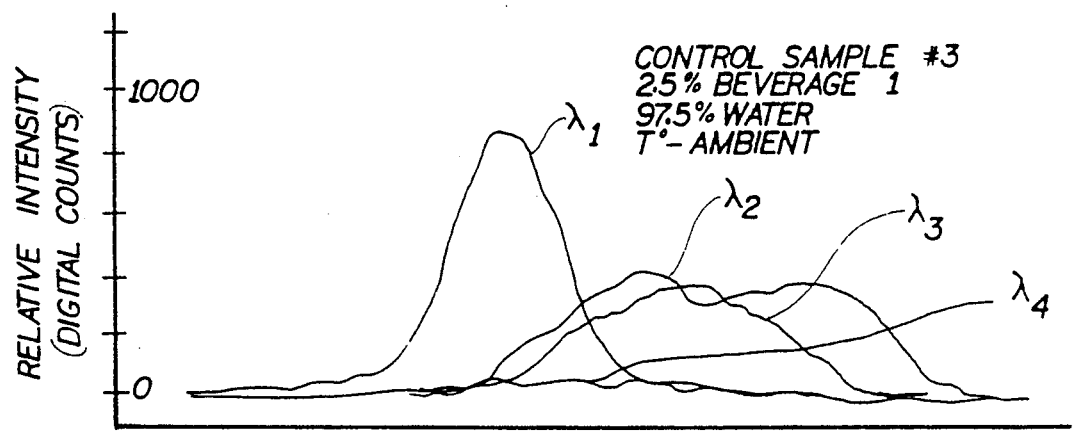
Figure 10D:
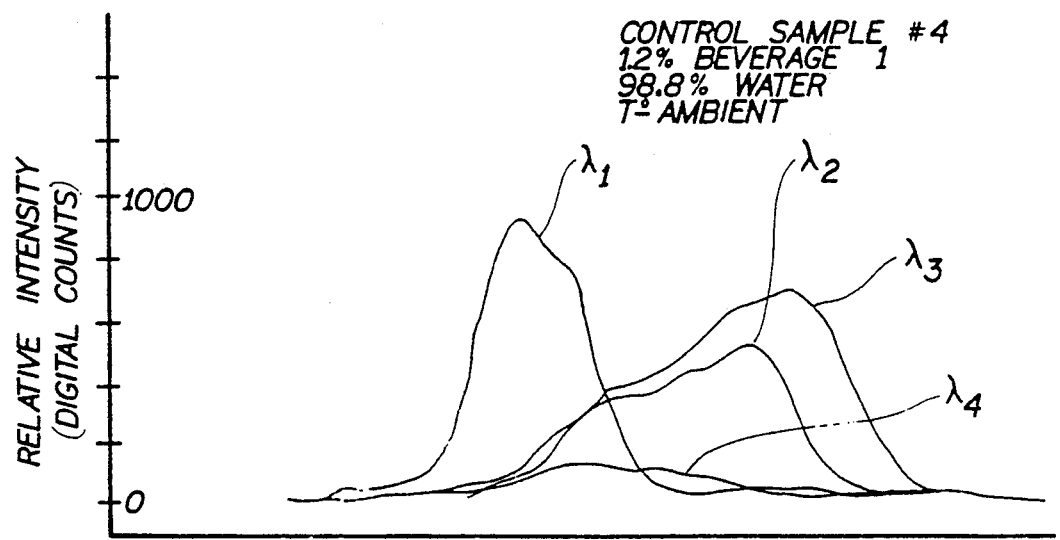
Figure 10E:
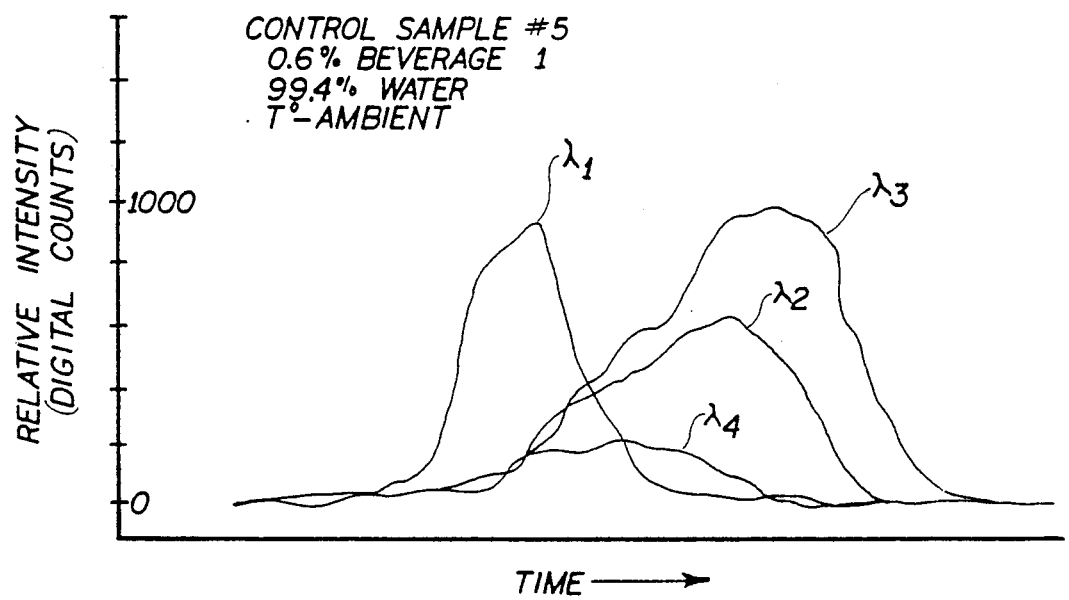
Figure 10F:
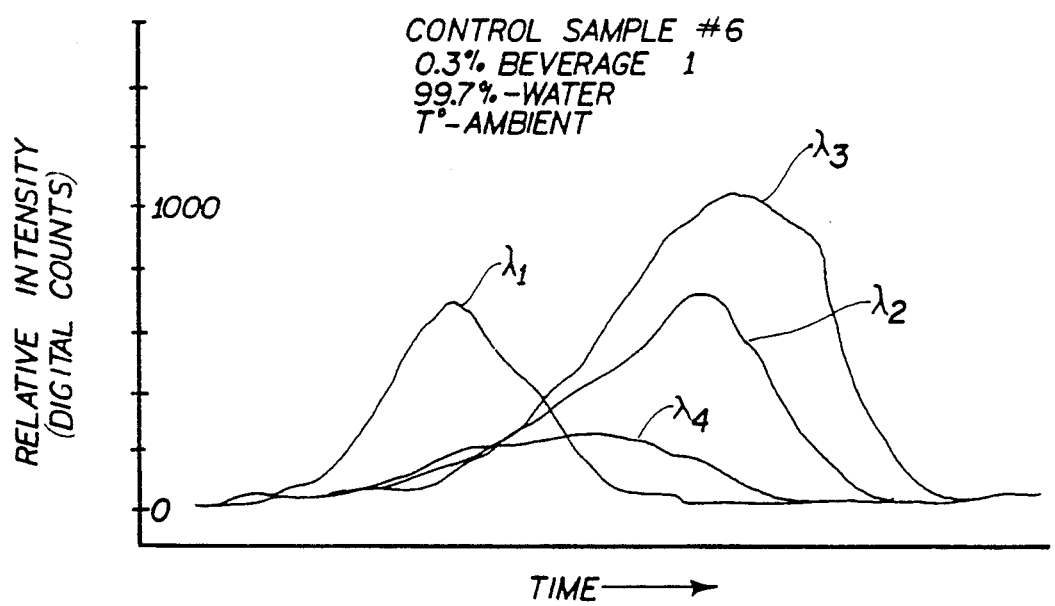

As seen in FIGS. 6 and 6A, the apparatus of the present invention comprises an illuminator module 30 and an emitter module 32 which cooperate to function as the light source 12. In one example, the illuminator module 30 is powered by a 5-volt, 3 amp power supply producing a 5 watt, light output from a quartz-halogen lamp 34, which light output is collected through collector lens 35 and focused by focusing lens 36 at the collecting end of a quartz, quartz-glass fiber optic cable 37, through which the collected and focused light is transmitted to the emitter module 32. The emitter module 32 comprises an aspherical, micro-lensed light source, which focuses a collimated, white light beam at the wall 39 of the fluid retaining medium 40, 40' and through the tested fluid 43 (control fluid or On-line Fluid). In the hereindisclosed embodiment of the referenced species, the apparatus is provided for the collection of transmitted light, rather than reflected or transflected. Thus, the light emitted from the emitting module 32 also passes through the opposite wall 41 of the fluid retaining medium 40, 40'. Non-absorbed light which is successfully transmitted through the fluid retaining medium 40, 40' and the fluid 43 is collected, as much as possible, at a collector module 45. It is between the emitter module 32 and collector module 45 that the apparatus differs significantly between the refillable container species and the flying brand species. The fluid retaining medium 40 of the refillable container species is a bottle 40 or other container. The apparatus of the refillable container species includes a bottle (or other container) holding and conveyor assembly 46 which holds a plurality of bottles 41 in spaced apart relationship and moves the bottles at a constant or semi-constant rate, progressively between the emitter module 32 and the collector module 45. In this refillable container species, the containers 40, be they bottles or plastic boxes, etc., comprise an integral component of the invented apparatus itself, functioning as the optical cell by integrating the container into the optics. The emitter module 32 of the residue detect species is adjustably mounted relative to the conveyor assembly 46 and fluid container 40 (as depicted by adjusting legs 31, 33) in order to adjustably direct the emitted light at and through the container and fluid 43 within the container. (See FIG. 9). The flying brand species, comprises, between the emitter module 32 and collector module 45 a fluid conduit (pipe) 40' which is the fluid retaining medium. The tested fluid 43 is pumped through the conduit 40'. The fluid conduit 40' is provided with transparent walls (observation ports) 48 at the section of conduit which is in line with the emitter module 32 and collector module 45, in order that emitted light from the emitter module passes through the transparent walls of the conduit, through the tested fluid 43 and on to the collector module 45. The effect which this distinction in fluid retaining mediums 40, 45 has on the performance of the method in each of the two species is discussed later.

The collector module 45 functions as the collector 14 (FIG. 5) of the invented apparatus and includes a collector lens 44 which collects, as much as possible, and focuses the transmitted light (or, in alternate embodiments, the reflected or transflected light) onto the collecting end of a second, quartz, quartz-glass fiber optic cable 17. This fiber optic cable 17 is devided (see previous discussion) into "n" segments $18\text{-}l \ldots 18\text{-}n$, each of which carries light to one of "n" filter modules $20\text{-}l \ldots 20\text{-}n$. Each filter module 20 includes a narrow band-pass quartz filler $49\text{-}l \ldots 49\text{-}n$ which filters the collected light carried by the respective cable segment $18\text{-}l \ldots 18\text{-}n$ into filtered light at one of the chosen, profiling wavelengths. Associated with each filter module $20\text{-}l \ldots 20\text{-}n$ is a photodiode light detector 51 and an amplifier 52. The photodiode 51 and amplifier 52 provide the function of the detector 22 and signal conditioning amplifier 24 (see FIG. 5) by converting the detected, filtered light to a voltage output directly proportional to its intensity. By way of example, only, the amplifier 52 is an 8261FET amplifier with feed-back and compensation resistors which cooperates with the photodiode 51 to provide a 0-N volt output signal which is directed along output cable 54 to a terminal $56a$–$56d$ at a terminal strip 55 for access by the recording device 26. In the preferred embodiments of the present, disclosed species, the recording device comprises a high-speed data acquisition system. One example of such data acquisition system includes the DAS, DT2800 board manufactured by Data Translation, and ASYST 1.53 Scientific Software package, compatible with the IBM® PC/AT with 8087 math co-processor. In this example, the DAS board 28 fits into a standard card slot of the IBM® AT or XT. The DAS digitizes the O-N volt analog signals from the filter/amplifier modules 20/24 utilizing direct memory access. After all data is acquired from a container 40 or group of containers or on a quantity of fluid 43 within a conduit 41', the processing device 26a calculates the chosen mathematical relationships among the data for each and all profiling wavelengths.

Figure 8:
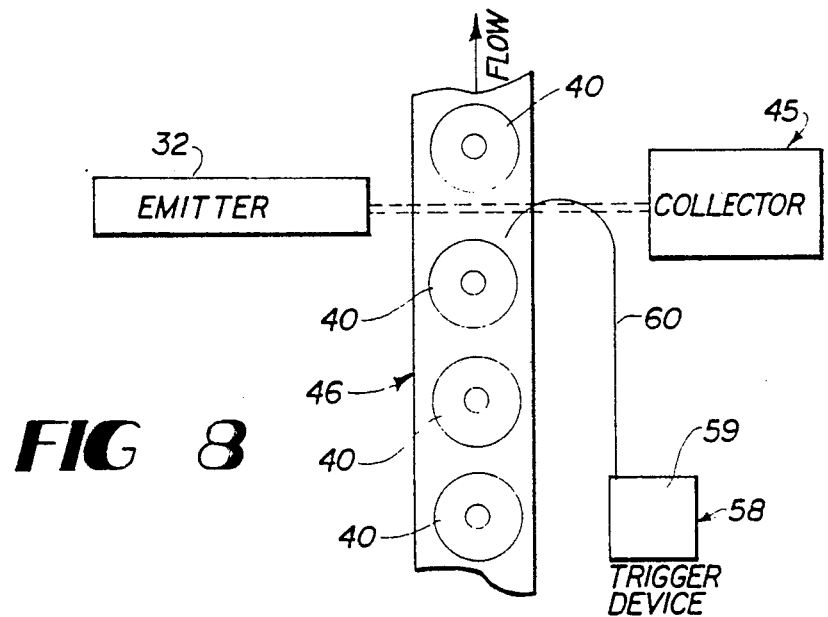
FIG. 8 is a schematic, top view representation of a trigger device in accordance with the embodiment of FIG. 6 of the present invention.

As indicated previously, data acquisition is accomplished, in the preferred embodiments, at a plurality of data acquisition points over a period of time referred to as the data acquisition period. With specific reference to the disclosed apparatus of FIGS. 6 and 6A, the light source 12 of these disclosed embodiments emits light continuously, during operation of the system, from the emitter module 32. The emitted light is continuously collected at the collector module 45 and conveyed to separate filter modules $20\text{-}l \ldots 20\text{-}n$, where the filtered light at each of the profiling wavelengths ($\lambda 1 - \lambda n$) is converted to an electrical signal (that is, a voltage). Thus a voltage potential is always present, during operation of the system, at each of the terminals 56a–56d of the terminal strip 55. In accordance with the preferred embodiments of the present invention, the voltages which are always present at the terminals 56a–56d are looked-at (or "acqisitioned") by the recording device 26 at intervals. These intervals define the data acquisition points and the data acquisition period ("AP"). See, for example, FIGS. 7 and 7A. The signatures of FIGS. 7 and 7A are defined by plotting the data acquired at each acquisition point. By way of example, the refillable container species includes a trigger device 58 which, in the disclosed embodiment, includes an electrical switch 59 (i.e. a micro-switch) activated by a trigger wire 60. (See FIG. 8.) The trigger device 58 is mounted at the conveyor assembly 46 at a point stationary relative to the emitter module 32 and collector module 45. Alignment is such that, as a container 40 enters the path of the emitted light, the container strikes the trigger wire 60 thus closing switch 59. The closed switch 59 is a signal to the recording device 26 to begin acquisitioning voltage data from the terminals 56a–56d. Thus, the recording device 26, functioning as a data acquisition system, systematically acquires and records the voltage data from each terminal 56a–56d at a plurality of points in time. For example, the DT2800 DAS board 28 looks at terminal 56a, then 56b, then 56c, then 56d to acquire a first data point for each profiling wavelength; the DAS board looks again at terminal 56a, then 56b, then 56c, then 56d to acquire a second data point for each profiling wavelength; and so on, until the container 40 leaves engagement with the trigger wire 60 at which time the data acquisition period ends as to that container.

As another container 40 engages the trigger wire 60, data as to each profiling wavelength is again acquired and recorded at a plurality of points in time over a data acquisition period for that container. It is within the scope of the present invention to provide other forms of trigger devices 58, such as, but not limited to, capacitive or proximity sensors, or optical devices like an electric eye, or timed triggers which activate Data acquisition automatically at intervals coordinated with the speed of the conveyor assembly 46. In the flying brand species, data acquisition periods are preferably triggered by automatic timing or manual triggering, but not limited thereto.

In the above described embodiment, data is acquired for each profiling wavelength in a sequential manner; that is, from terminal 56a, then 56b, then 56c, then 56d, wait time, then repeat. Thus, the staggered acquisition periods "AP" of FIGS. 7 and 7A. In alternate embodiments, utilizing other known data acquisition techniques data is acquired for each of the profiling wavelengths simultaneously at each data acquisition point; that is, from 56a, 56b, 56c, 56d simultaneously, record, wait time, repeat.

The processing steps of the preferred embodiment are accomplished through operation of a software program by the processing device 26a. Once the mathematical relationships to be calculated have been chosen, the particular software program can be readily provided by one with ordinary skill in the art.

The comparing step of the preferred embodiment is accomplished by manual (visual) comparison of On-line Data to Control Data or, more preferably, by a computer device 26b executing appropriate software to function as a comparator. In either event, the preferred comparison involves determining the amount of deviation by which the processed On-line Data deviates from the corresponding, processed Control Data. If a processed On-line Data point deviates from the corresponding, Control Data point by more than a chosen, acceptable deviation, the data is determined not to "fit", for example, (compare FIGS. 12A and 11A and FIGS. 12B and 11B). Furthermore, if a clear slope differential exists between the plotted, normalized (first or second) Control Data and the corresponding, plotted, normalized On-line Data, the data is determined not to "fit". (Compare, for examples, FIGS. 12C and 11C and FIGS. 12D and 11D.)

The plotted data, of the attached figures, are provided for example purposes only and are not to be construed as limiting the scope of the present invention. A brief explanation of two examples is provided below in order to give the reader a better "feel" for alternate methods of the present invention, which methods are clearly described above:

I. Example I.

In this example, the method of the present invention is utilized with the apparatus of the Refillable Container Species of FIG. 6 to determine if returned bottles contain contaminant.

STEP A—Non-contaminants are selected to be a family of nonalcoholic beverages such as a cola, lemon-lime, orange, diet cola. Water is chosen as a noncontaminant liquid.

STEP B—Using Spectrographic analysis as indicated with respect to FIG. 2, four profiling wavelengths have been determined to satisfactorily identify (or "Profile") and distinguish each of the non-contaminants. These profiling wavelengths are designated as $\lambda_1$, $\lambda_2$, $\lambda_3$, and $\lambda_4$. Appropriate filters 49-1 . . . 49-4 are placed in the filter modules 20-1 . . . 20-4.

STEP C1—The Control Fluid is defined as a solution of a selected beverage from the family of non-contaminants ("Beverage 1") and water in concentration of 5% beverage to water, at, for example, ambient temperature and placed in a clear, previously unused, plastic bottle of the type being returned.

STEP C2–C5—Control Data is acquired for the Control Sample as detailed above, with respect to FIG. 6. The data in the example is taken over time. That is, 100 different readings (data acquisition points) are taken of the intensity at each profiling wavelength over the data acquisition period. In this example, the data acquisition period is approximately 50 milli-seconds and the data acquisition points were every 500 micro-seconds. For example of the plotted Control Data, see FIG. 10A. In a preferred embodiment, each control sample is passed through the light source, and control data is collected, a number of times (i.e. 25 times) to acquire an average value at each acquisition point and, thus, an average profile and average signature in order to compensate for possible equipment inconsistencies and inconsistencies in container orientation.

STEP C6—The Control Sample is revised and Control Data is acquired for the revised sample. This step is repeated for numerous revised samples. The revisions of this example include changing concentration such that Control Data is acquired on Control Samples of 3.7%, 2.5%, 1.2%, 0.6% and 0.3% beverage to water, respectively, all at ambient temperature. (See plotted Control Data of FIGS. 10B–10F.) Revisions of this example do not include changing temperatures at each of the concentration levels.

STEP C7—The acquired Control Data is processed to provide a series of topographies of processed Control Data as depicted by the plots of FIGS. 11A-11D.

STEP D1—The On-line Fluid of this example is defined (prepared) by introducing water into each of the returned bottles 40 on the conveyor assembly 46 thus defining, in each bottle, an unknown fluid (such as a solution or mixture) of water and some unknown substance(S).

STEP D2-D5—On-line Data is acquired as to each bottle of On-line Fluid, in accordance with the above described procedures, as the conveyor moves the bottles past the trigger device 58 and the emitted light beam. The On-line data of each bottle of On-line Fluid is acquired over time as was the Control Data. For example of the plotted, On-line data for one bottle of On-line Fluid, see FIG. 12.

STEP D6—The acquired On-line Data for the respective bottle of On-line Fluid is processed in the same manner as the Control Data to provide processed, On-line Data as depicted by the plots of FIGS. 12A-12D.

Figure 11A:
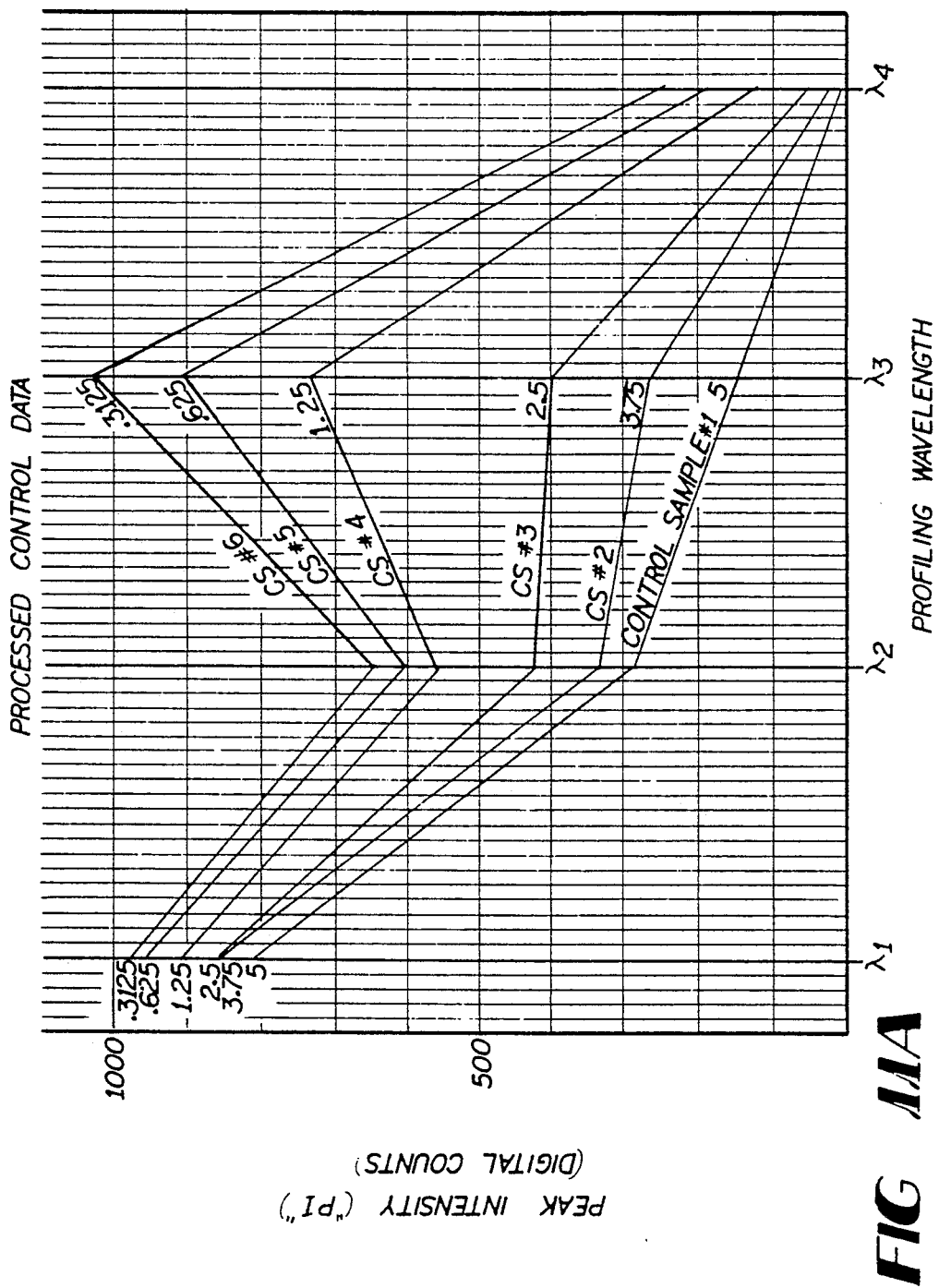
FIGS. 11A-11D are plotted representations of processed, Control Data of the specific examples of FIGS. 10A-10F.
Figure 11B:
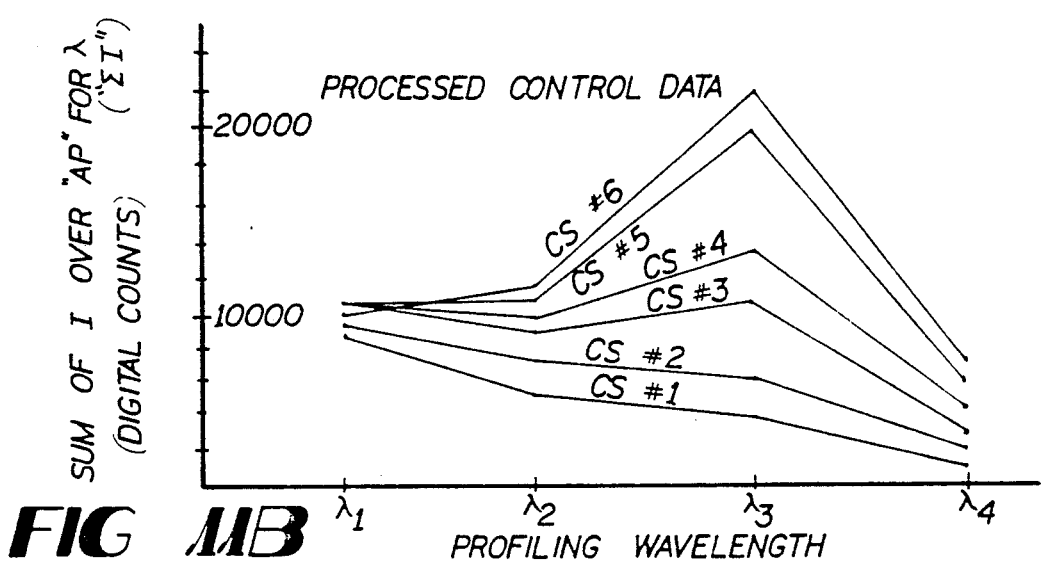
Figure 11C:
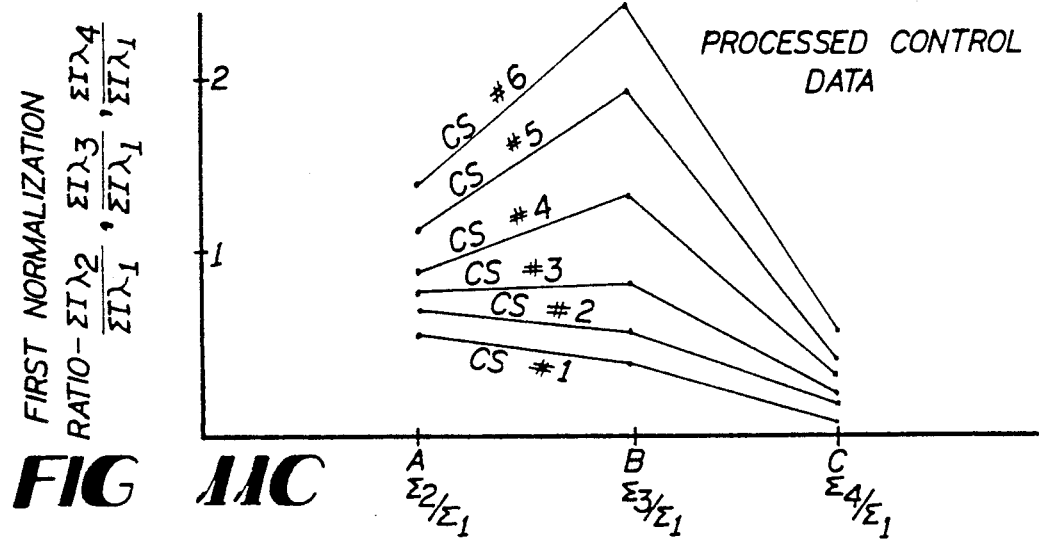
Figure 11D:
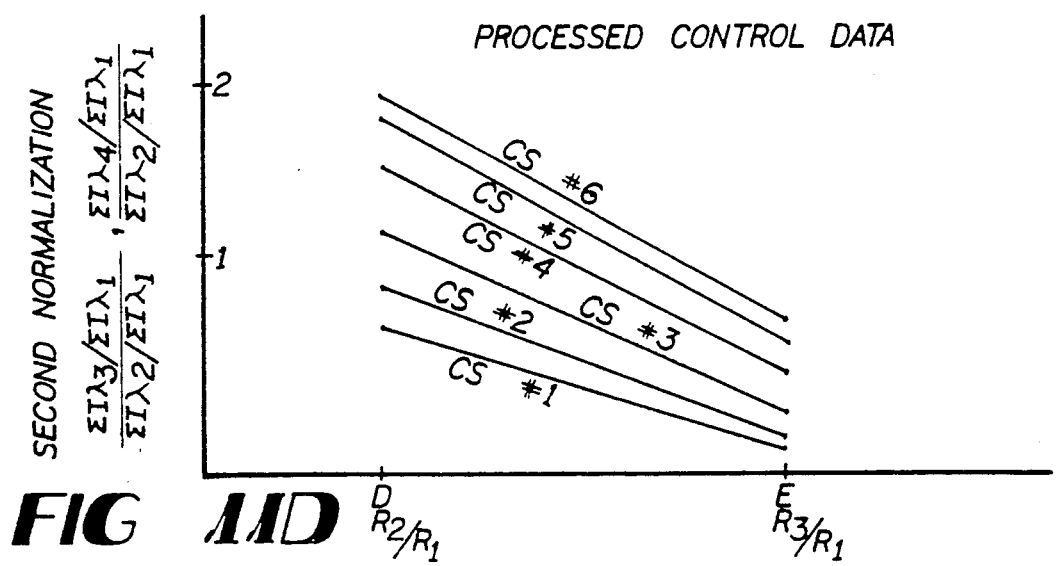
Figure 12A:
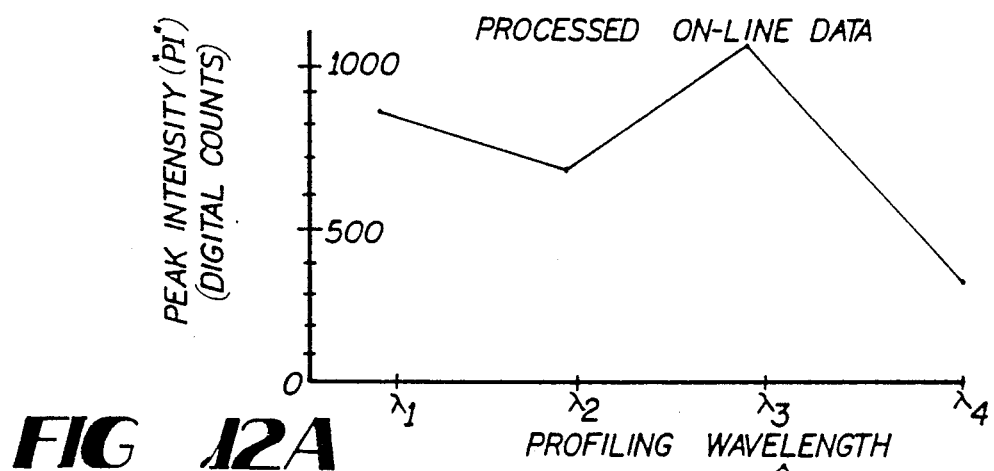
FIGS. 12A-12D are plotted representations of the processed, On-Line Data of the specific example of FIG. 12.
Figure 12B:
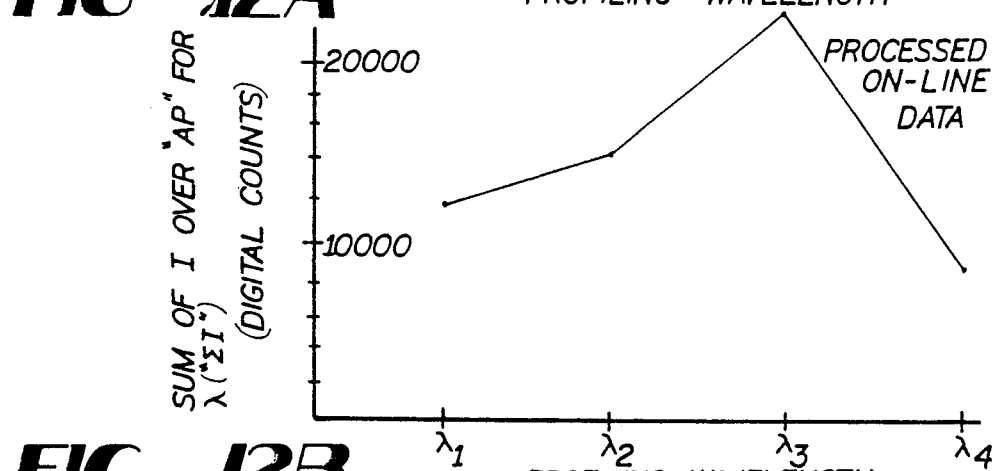
Figure 12C:
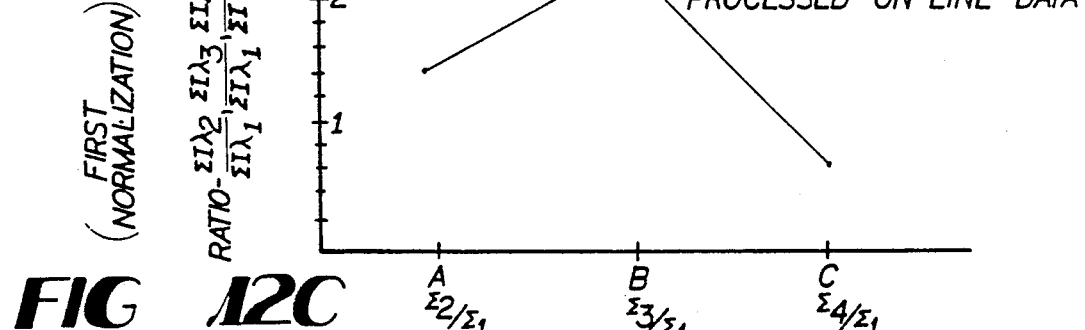
Figure 12D:
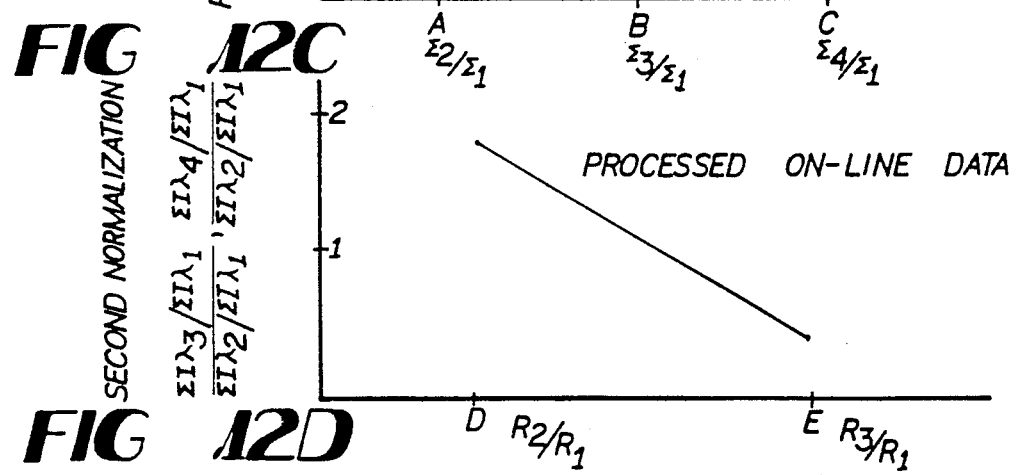
Figure 13:
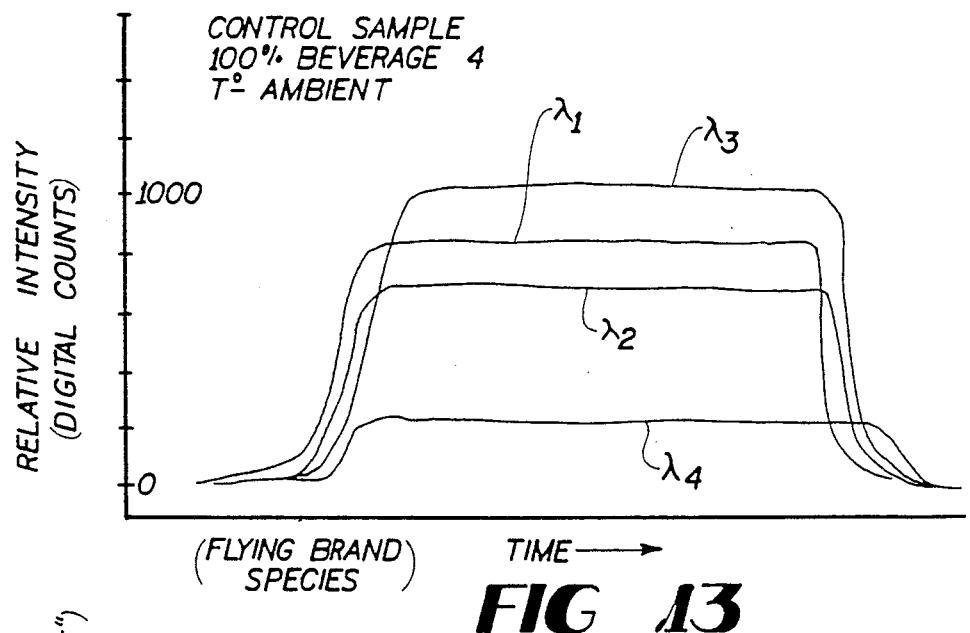
FIG. 13 is a plotted representation of Control Data acquired from a Control Sample, in accordance with the Flying Brand Species embodiment of FIG. 6A, and showing a specific example.

STEP E—The processed, On-line Data is compared to the processed, Control Data to "fit" within chosen deviations. In this example, one comparison is made between the peak to peak distances of the processed, On-line Data (FIGS. 12A, 12B) and of each signature within the respective topography (FIGS. 11A, 11B); another comparison is made between the slope of the first normalized and second normalized, processed data of the On-line Fluid FIGS. 12C, 12D) and the slope of corresponding, processed, Control Data or processed interpolated control data (FIGS. 11C, 11D).

STEP F—The On-line fluid in each bottle is, thus, determined to be contaminated or not.

STEP G—If determined to be contaminated, signal is, for example, directed to a reject mechanism 63 to remove the specific bottle from the conveyor assembly 46.

II. Example II.

In this example, the method of the present invention is utilized with the apparatus of the Flying Brand Species of FIG. 6A to determine if a fluid within the fluid conduit 40', at the point of the observation port 48, is the intended fluid (that is, the non-contaminant).

STEP A—The non-contaminant is identified to be a particular nonalcoholic beverage ("Beverage 4"). Other substances which will purposely be pumped through the conduit from time to time, such as Beverage 1, Beverage 2, Beverage 3 are, for purpose of this example, considered to be "Contaminants" since they are not the "intended fluid".

STEP B—Using Spectrographic Analysis, four, profiling wavelengths are ascertained which are determined to satisfactorily identify and distinguish the normal contaminants and non-contaminant. These profiling wavelengths are designated as $\lambda_1, \lambda_2, \lambda_3, \lambda_4$. Appropriate filters 49-1 ... 49-4 are placed in the filter modules 20-1 ... 20-4.

STEP C1—The Control Fluid is defined as 100% pure Beverage 4, and placed in the clean, purged conduit.

STEP C2-C5—Control Data is acquired for the Control Sample, as it passes the observation port 48, as detailed above with respect to FIG. 6A. The data is taken over time during an automatically or manually defined data acquisition period. There were 100 data acquisition points for each profiling wavelength. See FIG. 13 for an example of the plotted Control Data.

STEP C6—The Control Sample is not revised in this example. It was decided to use a control sample of only 100% pure Beverage at ambient temperature.

Figure 14A:
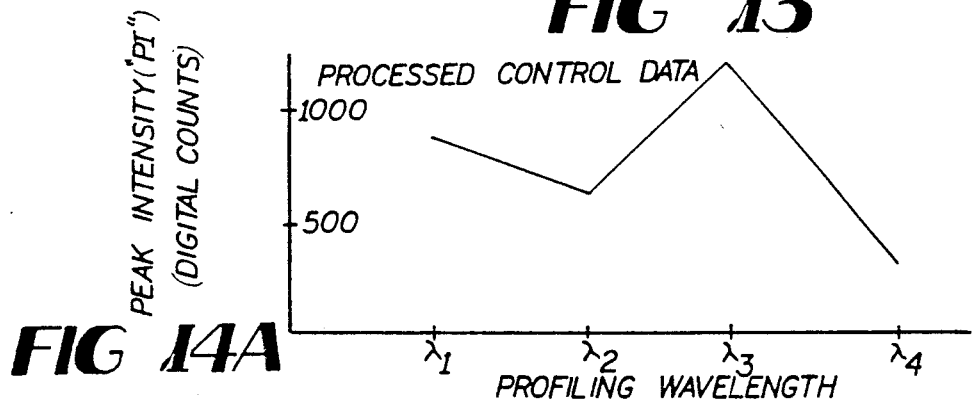
FIGS. 14A-14C are plotted representation of processed, Control Data of the specific example of FIG. 13.
Figure 14B:
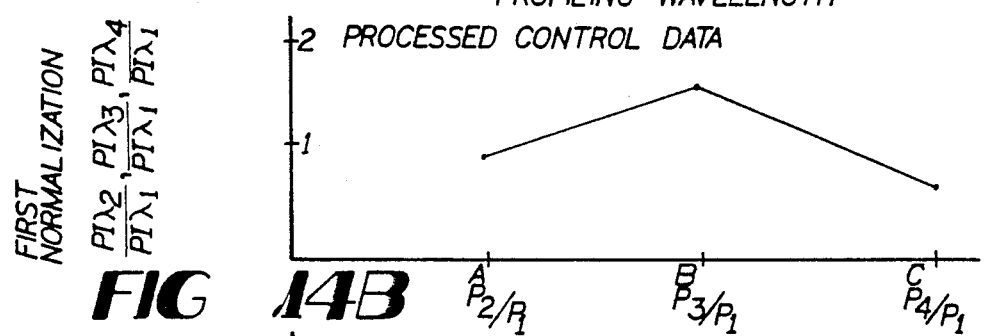
Figure 14C:
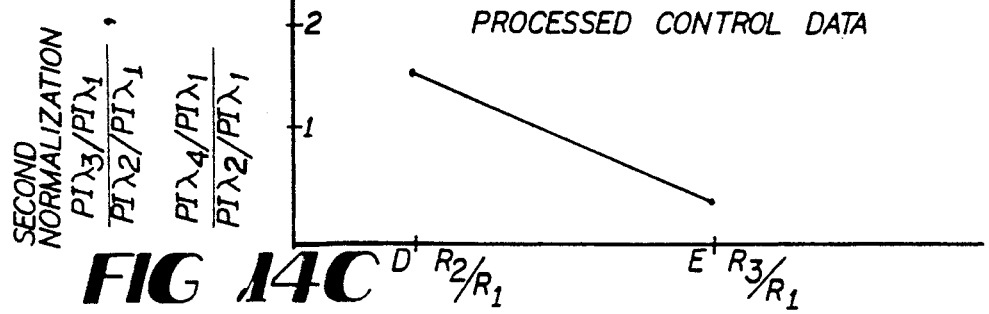

STEP C7—The acquired Control Data is processed to provide topographies of processed, Control Data as depicted by the plots of FIGS. 14A-14C.

STEP D1—During daily operation of the bottling facility, fluid is piped through the conduit 40' (preparation of the On-Line Fluid) on its way to consumer packaging 62 (see FIG. 6A). Whatever fluid is in the conduit 40' at a given time is defined as the On-line Fluid.

Figure 15:
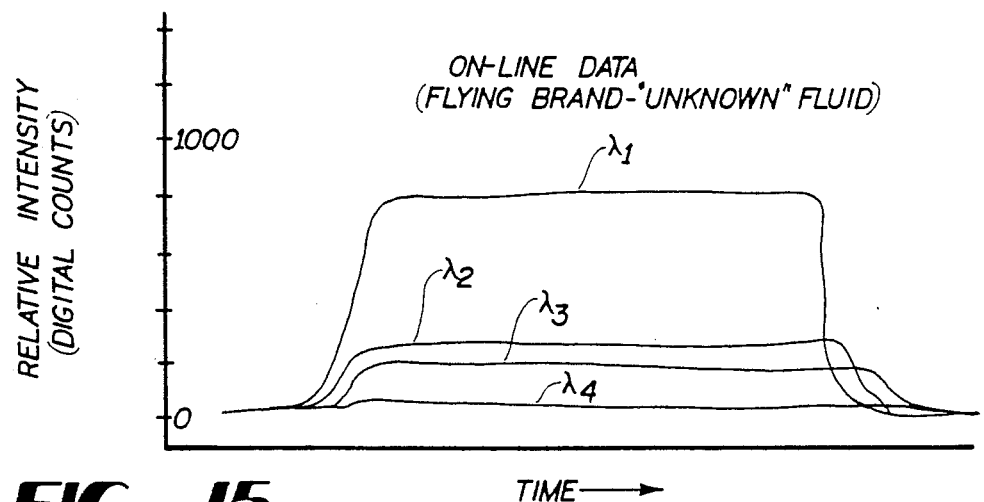
FIG. 15 is a plotted representation of On-line Data acquired from an On-line Sample, in accordance with the Flying Brand Species embodiment of FIG. 6A, and showing a specific example.

STEP D2-D5—On-line Data is acquired as to On-line Fluid in the conduit at any given time by automatically or manually activating the DAS Board 28, and, thus, the Data acquisition function of the apparatus of FIG. 6A, in accordance with the above described procedures. In this example, the data was acquired over a specific data acquisition period as was the Control Data. For example of the plotted, On-line Data for one acquisition period, see FIG. 15.

Figure 15A:
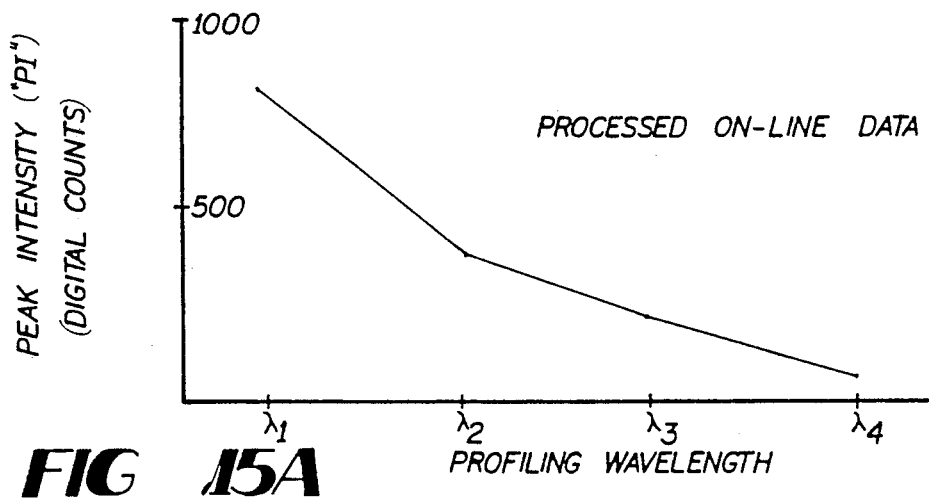
FIGS. 15A-15C are plotted representations of the processed, On-Line Data of the specific example of FIG. 15.
Figure 15B:
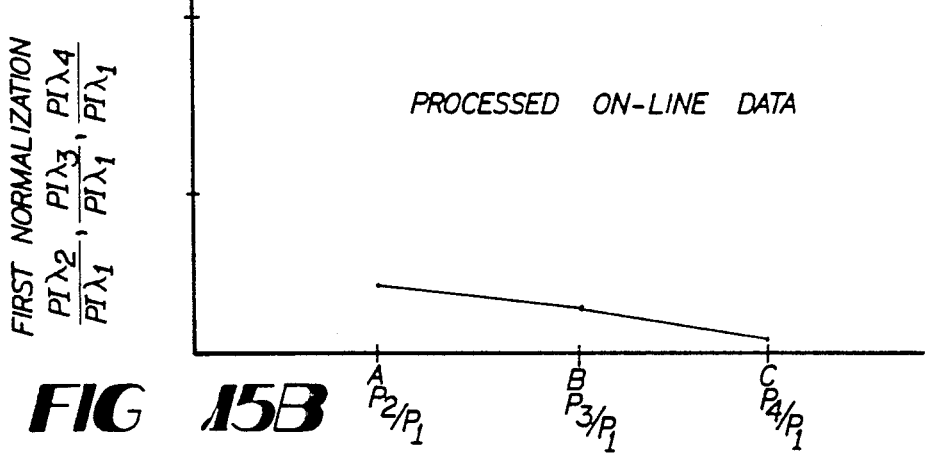
Figure 15C:
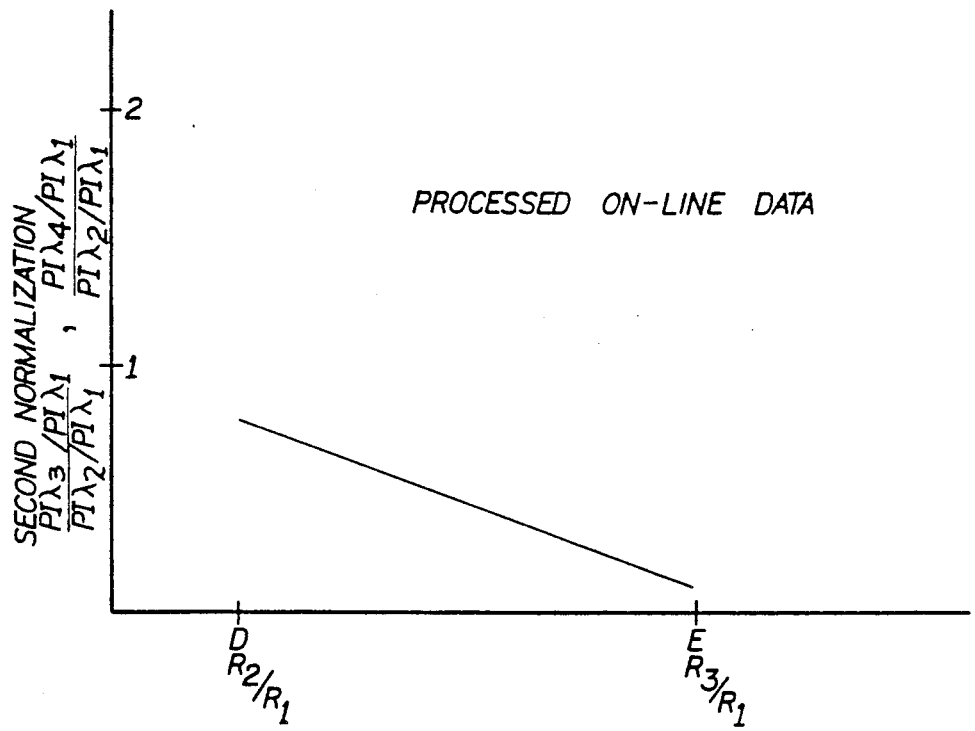

STEP D6—The acquired On-line Data for the Fluid at the observation port 48 at the given acquisition period is processed in the same manner as the Control Data to provide processed, On-line Data as depicted by the plots of FIGS. 15A-15C.

STEP E—The processed, On-line Data is compared to the processed Control Data to "fit" within chosen deviations. In this example, one comparison is made between the peak to peak distances of the processed, On-line Data (FIG. 14A) and of each signature within the topography of processed Control Data (FIG. 15A); another comparison is made between the slope of the first normalized and second normalized, processed data of the On-line Fluid (FIGS. 14B, 14C) and the slope of corresponding processed Control Data (FIGS. 15B, 15C).

STEP F—In the present example, the On-line Fluid passing the observation port 48, as represented by the sample data, is determined to be contaminated since it does not "fit" the control data; that is the fluid is not the 100% pure Beverage 4.

STEP G—Signal is directed to a flow control device 63' to channel the On-line Fluid away from the consumer packaging 62, for example to a waste drain 64 or alternate containers 64.

Figure 16:
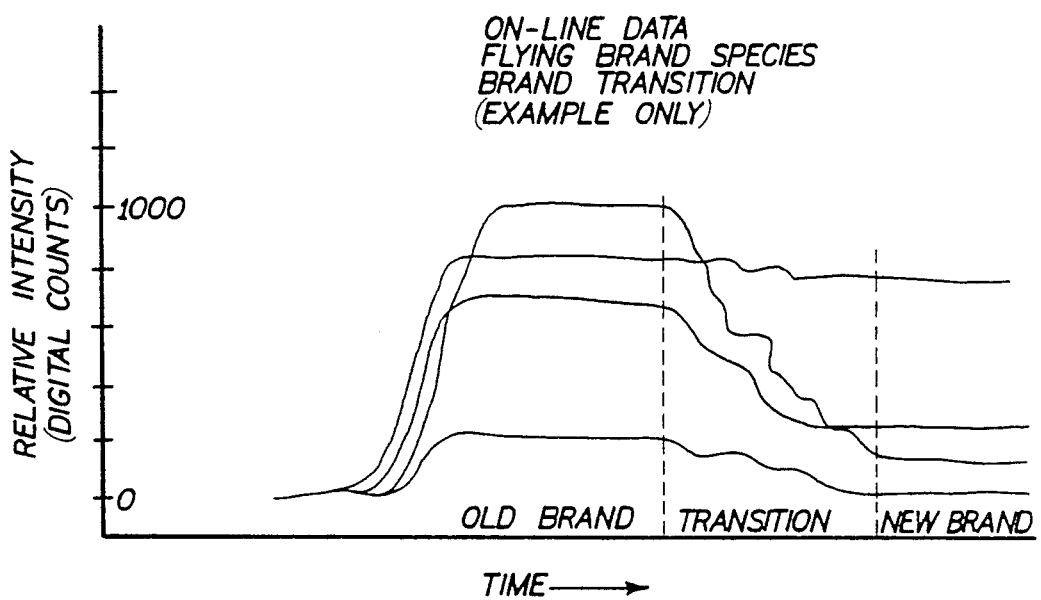
FIG. 16 is a plotted representation of on-Line Data acquired from an on-Line fluid, in accordance with an alternate application of the Flying Brand Species embodiment of FIG. 6A, and showing a specific example.

In still another alternate embodiment of the present invention, it is within the scope of the present invention, as practiced by the Flying Brand Species, to define an extended data acquisition period for acquiring On-line Data; for example, two or three hours. During that extended period, the resultant, filtered light at each of the profiling wavelengths is constantly monitored to record the intensity of light at each wavelength. If at any time during the data acquisition period, there is a change in intensity at one or more of the wavelengths, (see FIG. 16) which change exceeds a predetermined maximum, the apparatus of the present invention automatically determines that a change has occurred in the fluid 43 pumped through the conduit 40'. Upon such determination, appropriate flow controls are activated in accordance with a preplanned sequence.

Preferably, all control samples and on-Line samples are retained in containers 40 (reference the refillable container species) of a similar tint or color. Thus, in alternate embodiments of the present invention, one or more signal wavelengths are defined which correspond to the wavelengths of the tints of colored bottles other than the tint of the bottles used in the control samples.

For example, if control samples were retained in clear bottles, one signal wavelength would correspond to the green tint of a lemon-lime beverage container, etc. Upon detection of appropriate absorption in this (these) signal wavelength(s), during acquisition of On-Line data, the subject container is automatically routed in accordance with a preplanned control scheme, thus minimizing inaccuracies as to the relative intensities of the profiling wavelengths due to the container tint. In still alternate embodiments, collected, stored and processed control data includes data relating to control samples retained in various, differently tinted containers 40. Upon detection of appropriate absorption in one of the signal wavelengths during acquisition of On-Line data, the apparatus of the present invention selectively compares the processed On-Line data to processed control data from control samples retained in containers of the corresponding tint.

In still other, alternate embodiments of the present invention, a "servo channel" wavelength is defined at a point along the spectrum where absorption/scattering curves of all of the identified non-contaminants and selected contaminants are substantially similar. The Servo Channel is utilized to provide a method of compensating for intensity wavelength spectrum shifts. In this embodiment, the instrument (practicing the apparatus of the present invention) is periodically calibrated to a known standard (for example, DI water) by acquiring light intensity data at each of the profiling wavelengths and at the Servo wavelength, for the known standard. The intensity value for data acquired during this calibration step (the "pre-use value") is compared to the known value for the standard at each wavelength to calculate a gain factor ("G") for each profiling wavelength, and also for the Servo Channel. [G=known value/pre-use value.] The instrument is the placed in use to acquire control data and/or on-Line data in accordance with the present invention. The actual data value of intensity acquired at the Servo Channel is compared to the expected value at the Servo Channel to calculate a gain factor prime ("G'") to be applied universally to data at all wavelengths. That is, the "expected value" at the Servo Channel is the actual data acquired at the Servo Channel multiplied by the gain factor ("G"). [Thus, G'=expected value/actual value, at Servo Channel.] Thereafter, all intensity data actually acquired by the instrument is modified by multiplying the actual data by the respective G for the wavelength and then by G' to arrive at accurate data. [For example, $I\lambda_{n(accurate)} = I\lambda_{n(acquired)} \cdot G\lambda_n \cdot G'$].

Whereas the present invention has been described in detail with specific reference to particular embodiments thereof, it is understood that variations and modifications can be effected within the spirit and scope of the present invention as described and as defined in the appended Claims hereinbefore.

We claim:

1. Fluid inspection method, comprising the steps of:
   a. creating a control sample defining a known fluid, wherein the known fluid is a solution of a known non-contaminant and a known liquid in known concentrations;
   b. directing light from a light source at the control sample;
   c. collecting light after absorption of at least some of the light by the control sample;
   d. separating the collected light from the control sample into a plurality of pre-selected wavelengths;
   e. detecting the relative intensity of the collected light at each of the pre-selected wavelengths;
   f. collecting data associated with the control sample indicating, at least, relative intensities of the collected light at each of the preselected wavelengths;
   g. creating a modified control sample defining the known fluid modified as to one or both of the properties: (i) the concentration level of non-contaminant in solution; and/or (ii) the temperature of the control sample;
   h. repeating, for the modified control sample, the steps of directing light, collecting light, separating, detecting, collecting data, and creating a modified control sample; and
   i. processing the collected data to provide processed control data representative of a plurality of mathematical inter-relationships among the relative intensity data associated with the pre-selected wavelengths of each control sample;
   j. correlating the data of all control samples to provide at least a first "signature" which represents the known non-contaminant;
   k. directing light from a light source at a fluid to be tested;
   l. collecting light after absorption of at least some of the light by the test fluid;
   m. separating the collected light from the test fluid into a plurality of parts, each part having a preselected, characteristic wavelength being those same pre-selected wavelengths into which the collected light from the control sample was separated;
   n. detecting the relative intensity of the collected light from the test fluid at each of the selected wavelengths;
   o. collecting data associated with the test fluid indicating, at least, the relative intensities of the collected light at each of the preselected wavelengths;
   p. processing the collected data associated with the test fluid to provide processed data representative of a plurality of mathematical inter-relationships among the relative intensity data associated with the pre-selected wavelengths of the Test fluid;
   q. comparing the processed data for the test fluid to said signature which represents the known non-contaminant;
   r. determining from the comparison whether or not the tested fluid is unacceptably contaminated.

2. Method of claim 1, wherein the determining step comprises at least the step of determining that some substance dissimilar to the known fluid of the control sample is present in the tested fluid.

3. Method of claim 1, wherein the various steps of collecting light each includes, at least, the step of collecting the light after absorption at a plurality of test times within a predetermined test period; and wherein the various detecting steps each includes, at least, the step of detecting the relative intensity of the collected light at each of the selected wavelengths, at each of the test times.

4. Method of claim 3, wherein the various steps of processing data each comprise the steps of:
   processing the collected data to define at least a second category of data, which second category of data includes at least one of the following: (1) peak relative intensity ("PI") during the test period for each pre-selected wavelength ("$\lambda$"); or (2) the sum of the relative intensities ("$\epsilon I$") of all test times over the test period for each selected wavelength;

or (3) the area under a curve plotted by the coordinates of the relative intensities verses time for each selected wavelength; or (4) maximum average intensity ("AvI") over the test period for each selected wavelength; and processing said second category of data to define at least a third category of data, which third category of data includes data defined by normalizing second category data of each pre-selected wavelength to second category data of one of the pre-selected wavelengths as in the manner of $PI\lambda_2/PI\lambda_1$ and $PI\lambda_3/PI\lambda_1$ and $PI\lambda_n/PI\lambda_1$, or $\epsilon I\lambda_2/\epsilon I\lambda_1$ and $\epsilon I\lambda_3/\epsilon I\lambda_1$ and $\epsilon I\lambda_n/\epsilon I\lambda_1$, or $AvI\lambda_2/AvI\lambda_1$ and $AvI\lambda_3/AvI\lambda_1$ and $AvI\lambda_n/AvI\lambda_1$; and wherein the comparing step comprises, at least, the step of comparing the third category of data for the test fluid to similar data for the control sample.

5. Method of claim 4, further comprising the step of interpreting the third category of data to define at least a fourth category of data, which fourth category of data includes data defined by normalizing the third category data for each pre-selected wavelength to the third category data of one of the pre-selected wavelengths, as in the manner of $[PI\lambda_3/PI\lambda_1]/[PI\lambda_2/PI\lambda_1]$ and $[PI\lambda_n/PI\lambda_1]/[PI\lambda_2/PI\lambda_1]$ or $[\epsilon I\lambda_3/\epsilon I\lambda_1]/[\epsilon I\lambda_2/\epsilon I\lambda_1]$ and $[\epsilon I\lambda_n/\epsilon I\lambda_1]/[\epsilon I\lambda_2/\epsilon I\lambda_1]$ or $[AvI\lambda_3/AvI\lambda_1]/[AvI\lambda_2/AvI\lambda_1]$ and $[AvI\lambda_n/AvI\lambda_1]/[AvI\lambda_2/AvI\lambda_1]$; and wherein the comparing step comprises, at least, the step of comparing the fourth category data for the test fluid to similar data for the control sample.

6. Method of claim 1, further comprising the step of moving the test fluid past a stationary light source.

7. Method of claim 6, further comprising the step of constituting a test fluid in a container; wherein the container, with the fluid therein, is moved past the light source.

8. Method of claim 7, wherein the container is a plastic bottle.

9. Method of claim 6, wherein the test fluid is moved through a fluid conduit past the stationary light source.

10. Method of claim 1, further comprising the step of moving the light source past a standing test fluid.

11. Method of claim 10, further comprising the step of constituting a test fluid in a container; and wherein the light source is moved past the container with the fluid therein.

12. Method of claim 11, wherein the container is a plastic bottle.

13. Method of claim 1, further comprising the step of activating a reject mechanism in response to determining that the tested fluid is unacceptably contaminated.

14. Method of claim 1, wherein the various steps of directing light each include, at least, the step of directing a collimated light beam at the respective control sample or test fluid.

15. Method of claim 1, wherein each of the steps of directing light includes, at least, the steps of:

retaining the control samples and test fluid each in similar containers;

passing light into the container through a first wall portion of the container, into the respective control sample or test fluid retained in the container, and out of the container through a second wall portion of the container.

16. Method of claim 1, wherein each of the steps of collecting light includes, at least, one or more of the steps of;

collecting light transmitted through the respective control samples and test fluid;

collecting light reflected by the respective control samples and test fluid; and/or collecting light resulting from transflection of light directed at the respective control samples and test fluid.

17. Method of claim 1, wherein the signature provided in the correlating step is in the form of selectively associated, processed data stored within a computer medium.

18. Method of claim 17, wherein signature provided in the correlating step is in the form of a graphically displayed topography.

19. The method of claim 1, wherein the step of correlating data further comprises, at least, the step of correlating the data of all control samples to provide a plurality of "signatures", each signature representing the known non-contaminant by associating processed control data from control samples of different concentration levels at a common temperature or temperature range; and wherein the comparing step comprises, at least, the step of comparing the processed data for the test fluid to one or more of the signatures of the plurality of signatures.

20. The method of claim 1, wherein the step of correlating data further comprises, at least, the step of correlating the data of all control samples to provide a plurality of "signatures", each signature representing the known non-contaminant by associating processed control data from control samples of different temperature at a common concentration level; and wherein the comparing step comprises, at least, the step of comparing the processed data for the test fluid to one or more of the signatures of the plurality of signatures.

21. Method of claim 1, wherein each of the steps of collecting light includes, at least, one or more of the steps of;

collecting light transmitted through the respective control samples and test solution;

collecting light reflected by the respective control samples and test solution; and/or collecting light resulting from transflection of light directed at the respective control samples and test solution.

22. Fluid inspection method, said method comprising the steps of:

a. creating a plurality of control samples of a known, non-contaminated fluid, and b. modifying each control sample such that each said control sample differs from each of the other control samples by some property, while each control sample continues to consist essentially of the known non-contaminated fluid;

c. as to each control sample, directing light from a light source at the control sample;

d. as to each control sample, collecting light after absorption of at least some of the light by the control sample;

e. as to each control sample, separating the collected light from the control sample into a plurality of pre-selected wavelengths;

f. as to each control sample, detecting the relative intensity of the collected light from the control sample at each of the selected wavelengths;

g. as to each control sample, processing data representative of the detected relative intensities from the control sample to, at least, provide processed data representative of a plurality of mathematical inter-relationships among the relative intensity data associated with all of the selected wavelengths of the control sample;

h. correlating the processed data of two or more of the control samples of the plurality of control samples to provide at least a first control "topography" of processed control data which topography represents the known non-contaminated fluid;

h. directing light from a light source at a fluid to be tested;

i. collecting light after absorption of at least some of the light by the test fluid;

j. separating the collected light from the test fluid into a plurality of wavelengths, said wavelengths being those same pre-selected wavelengths into which the collected light from the control sample was separated;

k. detecting the relative intensity of the collected light from the test fluid at each of the selected wavelengths;

l. processing data representative of the detected relative intensities from the test fluid to, at least, provide processed data representative of a plurality of mathematical inter-relationships among the relative intensity data associated with all of the selected wavelengths of the test fluid;

m. comparing the processed data for the test fluid to the topography which represents the known non-contaminated fluid.

n. determining from the comparison whether or not the test fluid is unacceptably contaminated.

23. Method of claim 22, further comprising the step of constituting the test fluid in a container.

24. Method of claim 22, wherein the step of directing light includes, at least, the steps of directing a collimated light beam at the control sample and directing a collimated light beam at the test fluid.

25. Method of claim 22, further comprising the step of creating relative movement between the light source and the test fluid;

26. Method of claim 25, wherein the steps of directing light and creating a relative movement are interchangeable.

27. Method of claim 22, wherein the fluid to be tested is of uncertain make-up but consists, at least, of a known liquid, and wherein the non-contaminated fluid of the control sample is of known make-up, consisting essentially of a known non-contaminant and the same known liquid.

28. Method of claim 27, wherein the known liquid is water.

29. Method of claim 22, wherein the various steps of collecting light each includes, at least, the step of collecting the light after absorption at a plurality of test times within a predetermined test period; and wherein the various detecting steps each includes, at least, the step of detecting the relative intensity of the collected light at each of the selected wavelengths, at each of the test times, thereby defining a first category of data including, at least, coordinates of relative light intensity and test times for each of the selected wavelengths.

30. Method of claim 29, wherein the various steps of processing data each comprise the steps of:

processing the collected data to define at least a second category of data, which second category of data includes at least one of the following: (1) peak relative intensity ("PI") during the test period for each preselected wavelength ("$\lambda$"); or (2) the sum of the relative intensities ("$\epsilon I$") of all test times over the test period for each selected wavelength; or (3) the area (" ") under a curve plotted by the coordinates of the relative intensities verses time for each selected wavelength; or (4) maximum average intensity ("AvI") over the test period for each selected wavelength; and processing said second category of data to define at least a third category of data, which third category of data includes data defined by normalizing second category data of each pre-selected wavelength to second category data of one of the pre-selected wavelengths as in the manner of $PI\lambda_2/PI\lambda_1$ and $PI\lambda_3/PI\lambda_1$ and $PI\lambda_n/PI\lambda_1$, or $\epsilon I\lambda_2/\epsilon I\lambda_1$ and $\epsilon I\lambda_3/\epsilon I\lambda_1$ and $\epsilon I\lambda_n/\epsilon I\lambda_1$, or $AvI\lambda_2/AvI\lambda_1$ and $AvI\lambda_3/AvI\lambda_1$ and $AvI\lambda_n/AvI\lambda_1$; and wherein the comparing step comprises, at least, the step of comparing the third category of data for the test fluid to similar data for the control sample.

31. Method of claim 30, further comprising the step of interpreting the third category of data to define at least a fourth category of data, which fourth category of data includes data defined by normalizing the third category data for each pre-selected wavelength to the third category data of one of the pre-selected wavelengths, as in the manner of $$[PI\lambda_3/PI\lambda_1]/[PI\lambda_2/PI\lambda_1] \text{ and}$$

$$[PI\lambda_n/PI\lambda_1]/[PI\lambda_2/PI\lambda_1] \text{ or}$$

$$[\epsilon I\lambda_3/\epsilon I\lambda_1]/[\epsilon I\lambda_2/\epsilon I\lambda_1] \text{ and}$$

$$[\epsilon I\lambda_n/\epsilon I\lambda_1]/[\epsilon I\lambda_2/\epsilon I\lambda_1] \text{ or}$$

$$[AvI\lambda_3/AvI\lambda_1]/[AvI\lambda_2/AvI\lambda_1] \text{ and}$$

$$[AvI\lambda_n/AvI\lambda_1]/[AvI\lambda_2/AvI\lambda_1]; \text{ and}$$

wherein the comparing step comprises, at least, the step of comparing the fourth category data for the test fluid to similar data for the control sample.

32. Method of claim 22, wherein each processing step performed on each of the control samples of the plurality of control samples further comprises, at least, the step of correlating the processed data of the respective control sample to provide at least a first control "signature" associated with the respective control sample, and wherein the step of correlating the processed data of two or more control samples comprises, at least, the step of correlating the control signatures associated with two or more of the control samples to provide at least the first control topography.

33. Method of claim 32, wherein the step of processing data from the test fluid further comprises, at least the step of correlating the processed data of the test fluid to provide at least a first test "signature" which represents the fluid to be tested; and wherein the comparing step further comprises the step of comparing the test signature to one or more of the control signatures within at least the first topography.

34. Method of claim 33, wherein each of the correlating steps comprises the step of correlating the respective processed data or signatures to provide the respective signature or topography in the form of selectively associated, processed data stored within a computer medium.

35. Method of claim 33, wherein each of the correlating steps comprises the step of correlating the respective processed data or signatures to provide the respective signature or topography in graphically displayed format.

36. Method of claim 22, wherein each processing step performed on each of the control samples of the plurality of control samples further comprises, at least, the step of correlating the processed data of the respective control sample to provide a plurality of control signatures associated with the respective control sample, each control signature associated with each respective control sample relating processed control data representative of one of the mathematical interrelationship of the plurality of interrelationships, each control signature associated with each respective control sample differing from the other control signatures associated with that control sample as to the mathematical interrelationship represented; and wherein the step of correlating the processed data of two or more control samples to provide at least a first topography comprises the step of correlating the pluralities of control signatures associated with two or more control samples to provide a plurality of topographies of processed data which topographies each represent the known non-contaminated fluid.

37. Method of claim 36, wherein the step of processing data from the test fluid further comprises, at least the step of correlating the processed data of the test fluid to provide a plurality of test signatures, each signature of the plurality of test signatures relating processed test data representative of one of the mathematical interrelationships of the plurality of interrelationships, each test signature differing from the other test signatures as to the mathematical interrelationship represented; and wherein the comparing step further comprises the step of comparing the test signatures to the control signatures of one or more of the topographies.

38. Method of claim 37, wherein each of the correlating steps comprises the step of correlating the respective processed data or signatures to provide the respective signature or topography in the form of selectively associated, processed data stored within a computer medium.

39. Method of claim 37, wherein each of the correlating steps comprises the step of correlating the respective processed data or signatures to provide the respective signature or topography in graphically displayed format.

40. Method of claim 36, wherein each topography of the plurality of topographies relates signatures which represent similar mathematical relationships.

41. Method of claim 22, wherein the step of modifying each control sample comprises the step of modifying each respective control sample such that each control sample differs from each of the other control samples as to the temperature of the control sample.

42. Method of claim 22, wherein the step of creating a plurality of control samples comprises the step of creating a plurality of control samples of the known, non-contaminated fluid, which known, non-contaminated fluid of each said control sample consists essentially of the same known liquid and/or the same known, non-contaminant; and wherein the step of modifying each control sample comprises the step of modifying each control sample such that each said control sample differs from each of the other control samples by some property, while each control sample continues to consist essentially of the known non-contaminant and/or the known liquid; and wherein the correlating step comprises the step of correlating the processed data of two or more control samples of the plurality of control samples to provide at least a first "topography" of processed control data which topography represents the known non-contaminant; and wherein the comparing step comprises the step of comparing the processed data for the test fluid to the topography which represents the known non-contaminant.

43. Method of claim 42, wherein each processing step performed on each of the control samples of the plurality of control samples further comprises, at least, the step of correlating the processed data of the respective control sample to provide at least a first control "signature" associated with the respective control sample, and wherein the step of correlating the processed data of two or more control samples comprises, at least, the step of correlating the control signatures associated with two or more of the control samples to provide at least the first control topography.

44. Method of claim 43, wherein the step of processing data from the test fluid further comprises, at least the step of correlating the processed data of the test fluid to provide at least a first test "signature" which represents the fluid to be tested; and wherein the comparing step further comprises the step of comparing the test signature to one or more of the control signatures within at least the first topography.

45. Method of claim 44, wherein each of the correlating steps comprises the step of correlating the respective processed data or signatures to provide the respective signature or topography in the form of selectively associated, processed data stored within a computer medium.

46. Method of claim 44, wherein each of the correlating steps comprises the step of correlating the respective processed data or signatures to provide the respective signature or topography in graphically displayed format.

47. Method of claim 42, wherein each processing step performed on each of the control samples of the plurality of control samples further comprises, at least, the step of correlating the processed data of the respective control sample to provide a plurality of control signatures associated with the respective control sample, each control signature associated with each respective control sample relating processed control data representative of one of the mathematical interrelationship of the plurality of interrelationships, each control signature associated with each respective control sample differing from the other control signatures associated with that control sample as to the mathematical interrelationship represented; and wherein the step of correlating the processed data of two or more control samples to provide at least a first topography comprises the step of correlating the pluralities of control signatures associated with two or more control samples to provide a plurality of topographies of processed data which topographies each represent the known non-contaminated fluid.

48. Method of claim 47, wherein the step of processing data from the test fluid further comprises, at least the step of correlating the processed data of the test fluid to provide a plurality of test signatures, each signature of the plurality of test signatures relating processed test data representative of one of the mathematical interrelationships of the plurality of interrelationships, each test signature differing from the other test signatures as to the mathematical interrelationship represented; and wherein the comparing step further comprises the step of comparing the test signatures to the control signatures of one or more of the topographies.

49. Method of claim 48, wherein each of the correlating steps comprises the step of correlating the respective processed data or signatures to provide the respective signature or topography in the form of selectively associated, processed data stored within a computer medium.

50. Method of claim 48, wherein each of the correlating steps comprises the step of correlating the respective processed data or signatures to provide the respective signature or topography in graphically displayed format.

51. Method of claim 47, wherein each topography of the plurality of topographies relates signatures which represent similar mathematical relationships.

52. Method of claim 42, wherein the step of modifying each control sample comprises the step of modifying each respective control sample such that each control sample differs from each of the other control samples as to one or both of the properties of (i) relative concentrations of the known liquid and the known non-contaminant and/or (ii) the temperature of the control sample.

* * * * *